US009404118B2

(12) United States Patent
Köhler et al.

(10) Patent No.: US 9,404,118 B2
(45) Date of Patent: Aug. 2, 2016

(54) PICHIA CIFERRII CELLS AND USE THEREOF

(75) Inventors: Tim Köhler, Dorsten (DE); Christoph Schorsch, Frankfurt am Main (DE); Eckhard Boles, Darmstadt (DE); Heiko Andrea, Marl (DE); Mike Farwick, Essen (DE); Steffen Schaffer, Herten (DE)

(73) Assignee: EVONIK DEGUSSA GMBH, Essen (DE)

( * ) Notice: Subject to any disclaimer, the term of this patent is extended or adjusted under 35 U.S.C. 154(b) by 163 days.

(21) Appl. No.: 14/238,248

(22) PCT Filed: Jul. 23, 2012

(86) PCT No.: PCT/EP2012/064369
§ 371 (c)(1),
(2), (4) Date: Feb. 11, 2014

(87) PCT Pub. No.: WO2013/023878
PCT Pub. Date: Feb. 21, 2013

(65) Prior Publication Data
US 2014/0199736 A1    Jul. 17, 2014

(30) Foreign Application Priority Data
Aug. 18, 2011  (DE) .......................... 10 2011 110 959

(51) Int. Cl.
| | | |
|---|---|---|
| C12N 1/14 | (2006.01) | |
| C12N 15/81 | (2006.01) | |
| C07K 14/39 | (2006.01) | |
| C12N 9/04 | (2006.01) | |
| C12N 9/10 | (2006.01) | |
| C12N 9/12 | (2006.01) | |
| C12N 9/88 | (2006.01) | |
| C12P 13/02 | (2006.01) | |

(52) U.S. Cl.
CPC .............. *C12N 15/815* (2013.01); *C07K 14/39* (2013.01); *C12N 9/0006* (2013.01); *C12N 9/1014* (2013.01); *C12N 9/1029* (2013.01); *C12N 9/1205* (2013.01); *C12N 9/88* (2013.01); *C12P 13/02* (2013.01); *Y02P 20/52* (2015.11)

(58) Field of Classification Search
CPC .............................. C07K 14/39; C12N 9/0006
USPC ..................................... 435/128, 254.23, 471
See application file for complete search history.

(56) References Cited

U.S. PATENT DOCUMENTS

| | | | |
|---|---|---|---|
| 5,910,425 A | 6/1999 | De Boer et al. | |
| 8,372,595 B2 | 2/2013 | Schaffer et al. | |
| 2008/0299625 A1 | 12/2008 | Van Den Berg et al. | |
| 2010/0190219 A1 | 7/2010 | Schaffer et al. | |

FOREIGN PATENT DOCUMENTS

| | | |
|---|---|---|
| CN | 101098968 A | 1/2008 |
| CN | 101490260 A | 7/2009 |
| JP | 9-504434 | 5/1997 |
| JP | 2008-518612 A | 6/2008 |
| JP | 2009-536521 A | 10/2009 |
| KR | 10-2007-0091134 | 9/2007 |
| WO | WO 95/12683 A1 | 5/1995 |
| WO | WO 2006/048458 A2 | 5/2006 |
| WO | WO 2007131720 A1 | 11/2007 |

OTHER PUBLICATIONS

Written Opinion (237) PCT/EP2012/064369 (2012).*
Chinese Office Action issued in related Chinese Patent Application No. CN 201280039973.5 together with an English language translation.
Wickerham, Lynferd J. et al., "Formation of Extracellular Sphingolipides by Microorganisms", J. Bacteriol, Feb. 22, 1960, vol. 80, No. 4, pp. 484-491.
Ramos, Fernando et al., "Occurrence of a catabolic L-serine (L-threonine) deaminase in *Saccharomyces cerevisiae*", Eur J Biochem, Apr. 1982, vol. 123, No. 3, pp. 571-576.
Lanterman, Margaret M. et al., "Characterization of sphingosine kinase (SK) activity in *Saccharomyces cerevisiae* and isolation of SK-deficient mutants", Biochem J., Jun. 1, 1998, vol. 332, Pt. 2, pp. 525-531.
Van Veldhoven, Paul P. et al., "Subcellular localization and membrane topology of sphingosine-1-phosphate lyase in rat liver", J Biol Chem., Jul. 5, 1991, vol. 266, No. 19, pp. 12502-12507.
Devereux, John et al., "A comprehensive set of sequence analysis programs for the VAX", Nucleic Acid Research, Jan. 11, 1984, vol. 12 No. 1, pp. 387-395.
Altschul, Stephen F. et al., "Basic Local Alignment Search Tool", Journal of Molecular Biology, 1990, vol. 215, pp. 403-410.
Schorsch, Christoph et al., "Knockout of the DNA ligase IV homolog gene in the sphingoid base producing yeast Pichia ciferrii significantly increases gene targeting efficiency", Current Genetics, 2009, vol. 55, No. 4, pp. 381-389.
Zweerink, Marcia M. et al., "Characterization of a novel, potent, and specific inhibitor of serine palmitoyltransferase", J Biol Chem., Dec. 15, 1992, vol. 267, No. 35, pp. 25032-25038.
Grilley, Michelle M. et al., "Syringomycin Action Gene SYR2 Is Essential for Sphingolipid 4-Hydroxylation in *Saccharomyces cerevisiae*", J Biol Chem., May 1, 1998, vol. 273, No. 18, pp. 11062-11068.
Hermann, Thomas et al., "Proteome analysis of Corynebacterium glutamicum", Electrophoresis, May 2001, vol. 22, No. 9, pp. 1712-1723.
Lohaus, Christiane et al., "Proteomforschung", Biospektrum, 1989, vol. 5, pp. 32-39.
Lottspeich, "Ein Genom—verschiedene Proteome", Angewandte Chemie, 1999, vol. 111, pp. 2630-2647.

(Continued)

*Primary Examiner* — Tekchand Saidha
(74) *Attorney, Agent, or Firm* — Scully, Scott, Murphy & Presser, P.C.

(57) ABSTRACT

The invention relates to genetically modified *Pichia ciferrii* cells, to the use thereof and to a method of producing sphingoid bases and sphingolipids.

14 Claims, 2 Drawing Sheets

(56) References Cited

OTHER PUBLICATIONS

Figure 1:
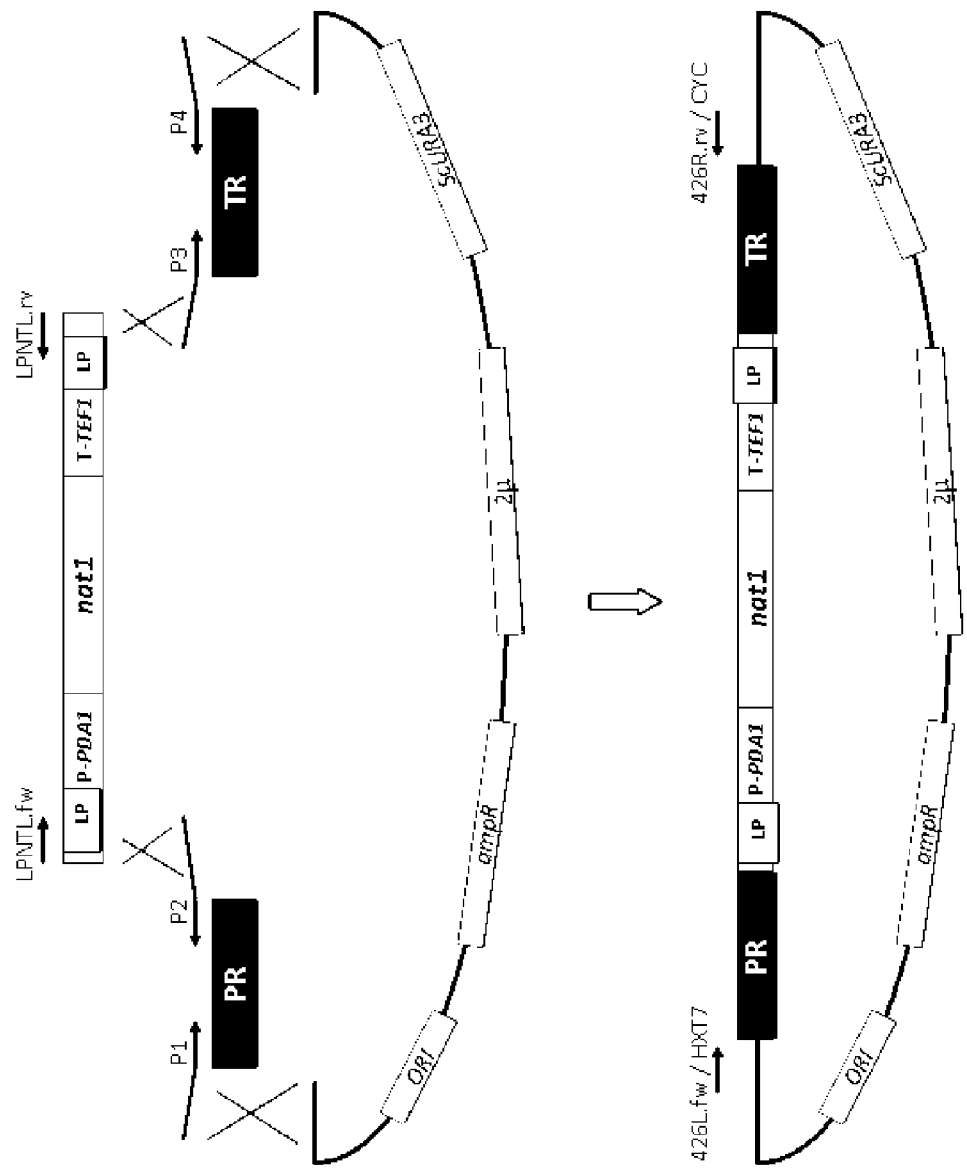

Rothstein, Rodney J., "[12] One-step gene disruption in yeast", Methods Enzymol, 1983, vol. 101, pp. 202-211.

Hamacher, Tanja et al., "Characterization of the xylose-transporting properties of yeast hexose transporters and their influence on xylose utilization" Microbiology, 2002, vol. 148, pp. 2783-2788.

Database EMBL [Online], May 21, 2010, "Sequence 10053 from Patent WO2010046221", XP002683376, retrieved from EBI accession No. EM_PAT:HC752962, Database accession No. HC752962.

Database EMBL [Online], Oct. 10, 2004, "Sequence 3361 from U.S. Pat. No. 6747137", XP002683377, retrieved from EBI accession No. EM_PAT:AR548230, Database accession No. AR548230.

Database Geneseq [Online], Jun. 1, 2006, "C. albicans cell wall protein CHA1-2 DNA SEQ ID No. 176", XP002683378, retrieved from EBI accession No. GSN:AEG97407, Database accession No. AEG97407.

Database EMBL [Online], Jan. 10, 2001, "T7 end of clone AT0AA004H05 of library AT0AA from strain CBS 4311 of *Saccharomyces servazzii*", XP002683379, retrieved from EBI access No. EM_GSS:AL402816, Database accession No. AL402816.

Database EMBL [Online], Apr. 16, 2009, "Sequence 4369 from Patent WO2009037279", XP002683380, retrieved from EBI accession No. EM_PAT:GN099588, Database accession No. GN099588.

Database EMBL [Online], Jul. 8, 2005, "cp56b06.r Candida parapsilosis Random Genomic Library Candida parapsilosis genomic clone cp56b06, genomic survey sequence", XP002683381, retrieved from EBI accession No. EM_GSS:CZ288060, Database accession No. CZ288060.

Schorsch, Christoph et al., "High-level production of tetraacetyl phytosphingosine (TAPS) by combined genetic engineering of sphingoid base biosynthesis and L-serine availability in the non-conventional yeast Pichia ciferrii", Metabolic Engineering (Mar. 1, 2012), vol. 14, No. 2, pp. 172-184.

German Office Action dated Mar. 28, 2012 issued in DE 10 2011 110 959.9.

Erläuterungen zu Abschnitt C. Ergebnis der Druckschriftenermittlung.

Bae, Jung-Noon et al., "Integrative Transformation System for the Metabolic Engineering of the Sphingoid Base-Producing Yeast Pichia ciferrii", Applied and Environmental Microbiology (Feb. 2003), vol. 69, No. 2, pp. 812-819.

International Search Report dated Sep. 26, 2012 issued in PCT/EP2012/064369.

Japanese Notice of Reasons for Rejection dated Dec. 10, 2015 received in Japanese Patent Application No. 2014-525378, together with an English-language translation.

* cited by examiner

SEQUENCE LISTING

```
<160> NUMBER OF SEQ ID NOS: 86

<210> SEQ ID NO 1
<211> LENGTH: 1347
<212> TYPE: DNA
<213> ORGANISM: Pichia ciferrii
<220> FEATURE:
<221> NAME/KEY: CDS
<222> LOCATION: (1)..(1347)

<400> SEQUENCE: 1 atg gct gaa atc ctt aaa aat gaa cgt cac aga caa aaa tca tca att      48
Met Ala Glu Ile Leu Lys Asn Glu Arg His Arg Gln Lys Ser Ser Ile
1               5                  10                  15 act tta att cca tca gaa aat ttt aca tca aaa tct gtt atg gat tta      96
Thr Leu Ile Pro Ser Glu Asn Phe Thr Ser Lys Ser Val Met Asp Leu
            20                  25                  30 tta ggt tca gaa atg caa aat aaa tat tca gaa ggt tat cca ggt gaa     144
Leu Gly Ser Glu Met Gln Asn Lys Tyr Ser Glu Gly Tyr Pro Gly Glu
        35                  40                  45 cgt tat tat ggt ggt aat gaa ttt att gat caa gct gaa gca tta tgt     192
Arg Tyr Tyr Gly Gly Asn Glu Phe Ile Asp Gln Ala Glu Ala Leu Cys
    50                  55                  60 caa aaa cgt gct ttg gaa gct ttt aac ttg gat cct gaa tta tgg gga     240
Gln Lys Arg Ala Leu Glu Ala Phe Asn Leu Asp Pro Glu Leu Trp Gly
65                  70                  75                  80 gtt aat gtt caa tct tta tca ggt gca cca gca aat tta tat gct tat     288
Val Asn Val Gln Ser Leu Ser Gly Ala Pro Ala Asn Leu Tyr Ala Tyr
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 85  |     |     |     |     | 90  |     |     |     |     | 95  |     |      |
| tca | tca | atc | tta | aat | gtt | ggt | gat | aga | att | atg | ggt | ctt | gat | tta | cct | 336  |
| Ser | Ser | Ile | Leu | Asn | Val | Gly | Asp | Arg | Ile | Met | Gly | Leu | Asp | Leu | Pro |      |
|     |     |     | 100 |     |     |     |     | 105 |     |     |     |     | 110 |     |     |      |
| cat | ggt | ggt | cat | tta | tct | cat | ggt | tat | caa | act | gct | aca | act | aaa | atc | 384  |
| His | Gly | Gly | His | Leu | Ser | His | Gly | Tyr | Gln | Thr | Ala | Thr | Thr | Lys | Ile |      |
|     |     | 115 |     |     |     |     | 120 |     |     |     |     | 125 |     |     |     |      |
| tct | tat | att | tca | aaa | tat | ttc | caa | act | atg | cca | tat | aga | tta | aat | gaa | 432  |
| Ser | Tyr | Ile | Ser | Lys | Tyr | Phe | Gln | Thr | Met | Pro | Tyr | Arg | Leu | Asn | Glu |      |
|     | 130 |     |     |     |     | 135 |     |     |     |     | 140 |     |     |     |     |      |
| gaa | act | ggt | ata | att | gat | tat | gat | gca | tta | gaa | aaa | tct | gca | gaa | tta | 480  |
| Glu | Thr | Gly | Ile | Ile | Asp | Tyr | Asp | Ala | Leu | Glu | Lys | Ser | Ala | Glu | Leu |      |
| 145 |     |     |     |     | 150 |     |     |     |     | 155 |     |     |     |     | 160 |      |
| ttt | aga | cca | aaa | atc | att | gtt | gca | ggt | gct | tca | gca | tat | tca | aga | att | 528  |
| Phe | Arg | Pro | Lys | Ile | Ile | Val | Ala | Gly | Ala | Ser | Ala | Tyr | Ser | Arg | Ile |      |
|     |     |     |     | 165 |     |     |     |     | 170 |     |     |     |     | 175 |     |      |
| att | gat | tat | gaa | aga | atc | aag | aaa | atc | gca | gat | aaa | gtt | aat | gct | tat | 576  |
| Ile | Asp | Tyr | Glu | Arg | Ile | Lys | Lys | Ile | Ala | Asp | Lys | Val | Asn | Ala | Tyr |      |
|     |     |     | 180 |     |     |     |     | 185 |     |     |     |     | 190 |     |     |      |
| gtg | cta | tca | gat | atg | gct | cat | att | tca | ggt | tta | gtt | tct | gca | gaa | gtt | 624  |
| Val | Leu | Ser | Asp | Met | Ala | His | Ile | Ser | Gly | Leu | Val | Ser | Ala | Glu | Val |      |
|     |     | 195 |     |     |     |     | 200 |     |     |     |     | 205 |     |     |     |      |
| aca | cca | tca | cca | ttc | cca | ttc | tca | gat | att | gtt | act | aca | aca | act | cat | 672  |
| Thr | Pro | Ser | Pro | Phe | Pro | Phe | Ser | Asp | Ile | Val | Thr | Thr | Thr | Thr | His |      |
|     | 210 |     |     |     |     | 215 |     |     |     |     | 220 |     |     |     |     |      |
| aaa | tca | tta | aga | ggt | cca | aga | ggt | gca | atg | att | ttc | ttt | aga | aaa | ggt | 720  |
| Lys | Ser | Leu | Arg | Gly | Pro | Arg | Gly | Ala | Met | Ile | Phe | Phe | Arg | Lys | Gly |      |
| 225 |     |     |     |     | 230 |     |     |     |     | 235 |     |     |     |     | 240 |      |
| tta | aga | aaa | act | act | aaa | aag | ggt | aaa | gaa | att | tat | tat | gat | tta | gaa | 768  |
| Leu | Arg | Lys | Thr | Thr | Lys | Lys | Gly | Lys | Glu | Ile | Tyr | Tyr | Asp | Leu | Glu |      |
|     |     |     |     | 245 |     |     |     |     | 250 |     |     |     |     | 255 |     |      |
| aaa | aaa | att | aat | ttt | tct | gtt | ttc | cca | gct | cat | caa | ggt | ggt | cca | cat | 816  |
| Lys | Lys | Ile | Asn | Phe | Ser | Val | Phe | Pro | Ala | His | Gln | Gly | Gly | Pro | His |      |
|     |     |     | 260 |     |     |     |     | 265 |     |     |     |     | 270 |     |     |      |
| aat | cat | aca | att | tct | gca | tta | gct | gtt | gct | ttg | aaa | caa | gca | caa | tct | 864  |
| Asn | His | Thr | Ile | Ser | Ala | Leu | Ala | Val | Ala | Leu | Lys | Gln | Ala | Gln | Ser |      |
|     |     | 275 |     |     |     |     | 280 |     |     |     |     | 285 |     |     |     |      |
| tca | gaa | tat | aaa | gaa | tat | caa | caa | aat | gtt | gtt | aat | aat | gca | agt | cat | 912  |
| Ser | Glu | Tyr | Lys | Glu | Tyr | Gln | Gln | Asn | Val | Val | Asn | Asn | Ala | Ser | His |      |
|     | 290 |     |     |     |     | 295 |     |     |     |     | 300 |     |     |     |     |      |
| ttc | gct | gat | gtt | tta | caa | aca | aaa | ggt | ttt | gat | tta | gtt | tct | aat | ggt | 960  |
| Phe | Ala | Asp | Val | Leu | Gln | Thr | Lys | Gly | Phe | Asp | Leu | Val | Ser | Asn | Gly |      |
| 305 |     |     |     |     | 310 |     |     |     |     | 315 |     |     |     |     | 320 |      |
| aca | gat | act | cat | tta | atc | ttg | att | gat | tta | cgt | tcc | aaa | aaa | att | gat | 1008 |
| Thr | Asp | Thr | His | Leu | Ile | Leu | Ile | Asp | Leu | Arg | Ser | Lys | Lys | Ile | Asp |      |
|     |     |     |     | 325 |     |     |     |     | 330 |     |     |     |     | 335 |     |      |
| ggt | gca | aga | tta | gaa | gct | gtt | tta | gaa | aga | ata | aac | att | gca | gct | aat | 1056 |
| Gly | Ala | Arg | Leu | Glu | Ala | Val | Leu | Glu | Arg | Ile | Asn | Ile | Ala | Ala | Asn |      |
|     |     |     | 340 |     |     |     |     | 345 |     |     |     |     | 350 |     |     |      |
| aaa | aat | act | att | cca | ggt | gat | aaa | tct | gct | tta | ttc | cca | tca | ggt | tta | 1104 |
| Lys | Asn | Thr | Ile | Pro | Gly | Asp | Lys | Ser | Ala | Leu | Phe | Pro | Ser | Gly | Leu |      |
|     |     | 355 |     |     |     |     | 360 |     |     |     |     | 365 |     |     |     |      |
| aga | gtt | ggt | act | cca | gca | atg | aca | aca | aga | ggt | ttt | gaa | aat | aaa | gaa | 1152 |
| Arg | Val | Gly | Thr | Pro | Ala | Met | Thr | Thr | Arg | Gly | Phe | Glu | Asn | Lys | Glu |      |
|     | 370 |     |     |     |     | 375 |     |     |     |     | 380 |     |     |     |     |      |
| ttt | aat | aaa | gtt | gca | gat | tat | att | gat | cgt | gct | gtt | aaa | tta | gct | ttg | 1200 |
| Phe | Asn | Lys | Val | Ala | Asp | Tyr | Ile | Asp | Arg | Ala | Val | Lys | Leu | Ala | Leu |      |
| 385 |     |     |     |     | 390 |     |     |     |     | 395 |     |     |     |     | 400 |      |
| att | tta | aaa | gat | caa | gct | aaa | ggt | gat | gat | gca | aga | gct | tta | tta | gca | 1248 |

```
                Ile Leu Lys Asp Gln Ala Lys Gly Asp Asp Ala Arg Ala Leu Leu Ala
                                405                 410                 415 aat ttc aaa aaa tta gct gat gaa tct gat gat gtt aaa gct tta ggt        1296
Asn Phe Lys Lys Leu Ala Asp Glu Ser Asp Asp Val Lys Ala Leu Gly
            420                 425                 430 aaa gaa gtt gct gaa tgg gtt tct caa tat cca gtt cca ggt gaa tta        1344
Lys Glu Val Ala Glu Trp Val Ser Gln Tyr Pro Val Pro Gly Glu Leu
        435                 440                 445 taa                                                                    1347

<210> SEQ ID NO 2
<211> LENGTH: 448
<212> TYPE: PRT
<213> ORGANISM: Pichia ciferrii

<400> SEQUENCE: 2

Met Ala Glu Ile Leu Lys Asn Glu Arg His Arg Gln Lys Ser Ser Ile
1               5                   10                  15

Thr Leu Ile Pro Ser Glu Asn Phe Thr Ser Lys Ser Val Met Asp Leu
            20                  25                  30

Leu Gly Ser Glu Met Gln Asn Lys Tyr Ser Glu Gly Tyr Pro Gly Glu
        35                  40                  45

Arg Tyr Tyr Gly Gly Asn Glu Phe Ile Asp Gln Ala Glu Ala Leu Cys
    50                  55                  60

Gln Lys Arg Ala Leu Glu Ala Phe Asn Leu Asp Pro Glu Leu Trp Gly
65                  70                  75                  80

Val Asn Val Gln Ser Leu Ser Gly Ala Pro Ala Asn Leu Tyr Ala Tyr
                85                  90                  95

Ser Ser Ile Leu Asn Val Gly Asp Arg Ile Met Gly Leu Asp Leu Pro
            100                 105                 110

His Gly Gly His Leu Ser His Gly Tyr Gln Thr Ala Thr Thr Lys Ile
        115                 120                 125

Ser Tyr Ile Ser Lys Tyr Phe Gln Thr Met Pro Tyr Arg Leu Asn Glu
    130                 135                 140

Glu Thr Gly Ile Ile Asp Tyr Asp Ala Leu Glu Lys Ser Ala Glu Leu
145                 150                 155                 160

Phe Arg Pro Lys Ile Ile Val Ala Gly Ala Ser Ala Tyr Ser Arg Ile
                165                 170                 175

Ile Asp Tyr Glu Arg Ile Lys Lys Ile Ala Asp Lys Val Asn Ala Tyr
            180                 185                 190

Val Leu Ser Asp Met Ala His Ile Ser Gly Leu Val Ser Ala Glu Val
        195                 200                 205

Thr Pro Ser Pro Phe Pro Phe Ser Asp Ile Val Thr Thr Thr Thr His
    210                 215                 220

Lys Ser Leu Arg Gly Pro Arg Gly Ala Met Ile Phe Phe Arg Lys Gly
225                 230                 235                 240

Leu Arg Lys Thr Thr Lys Lys Gly Lys Glu Ile Tyr Tyr Asp Leu Glu
                245                 250                 255

Lys Lys Ile Asn Phe Ser Val Phe Pro Ala His Gln Gly Gly Pro His
            260                 265                 270

Asn His Thr Ile Ser Ala Leu Ala Val Ala Leu Lys Gln Ala Gln Ser
        275                 280                 285

Ser Glu Tyr Lys Glu Tyr Gln Gln Asn Val Val Asn Asn Ala Ser His
    290                 295                 300

Phe Ala Asp Val Leu Gln Thr Lys Gly Phe Asp Leu Val Ser Asn Gly
```

```
                        305                 310                 315                 320
                Thr Asp Thr His Leu Ile Leu Ile Asp Leu Arg Ser Lys Lys Ile Asp
                                    325                 330                 335

Gly Ala Arg Leu Glu Ala Val Leu Glu Arg Ile Asn Ile Ala Ala Asn
                                340                 345                 350

Lys Asn Thr Ile Pro Gly Asp Lys Ser Ala Leu Phe Pro Ser Gly Leu
                            355                 360                 365

Arg Val Gly Thr Pro Ala Met Thr Thr Arg Gly Phe Glu Asn Lys Glu
                        370                 375                 380

Phe Asn Lys Val Ala Asp Tyr Ile Asp Arg Ala Val Lys Leu Ala Leu
                385                 390                 395                 400

Ile Leu Lys Asp Gln Ala Lys Gly Asp Asp Ala Arg Ala Leu Leu Ala
                                    405                 410                 415

Asn Phe Lys Lys Leu Ala Asp Glu Ser Asp Asp Val Lys Ala Leu Gly
                                420                 425                 430

Lys Glu Val Ala Glu Trp Val Ser Gln Tyr Pro Val Pro Gly Glu Leu
                            435                 440                 445

<210> SEQ ID NO 3
<211> LENGTH: 1410
<212> TYPE: DNA
<213> ORGANISM: Pichia ciferrii
<220> FEATURE:
<221> NAME/KEY: CDS
<222> LOCATION: (1)..(1410)

<400> SEQUENCE: 3 atg cca tac gct tta cca gaa tct cac aga caa tta gtc gaa ggt cat        48
Met Pro Tyr Ala Leu Pro Glu Ser His Arg Gln Leu Val Glu Gly His
1               5                   10                  15 tta aaa gat acc gat cca gaa gtt gaa caa atc att aaa gat gaa att        96
Leu Lys Asp Thr Asp Pro Glu Val Glu Gln Ile Ile Lys Asp Glu Ile
                20                  25                  30 gaa cgt caa aga cat tca atc gtc tta att gca tca gaa aat ttc act       144
Glu Arg Gln Arg His Ser Ile Val Leu Ile Ala Ser Glu Asn Phe Thr
            35                  40                  45 tca act gct gtt ttc gat gct tta gga act cca atg tgt aat aaa tat       192
Ser Thr Ala Val Phe Asp Ala Leu Gly Thr Pro Met Cys Asn Lys Tyr
        50                  55                  60 tct gaa ggt tat cca ggt gca aga tat tat ggt ggt aat gaa cat att       240
Ser Glu Gly Tyr Pro Gly Ala Arg Tyr Tyr Gly Gly Asn Glu His Ile
65                  70                  75                  80 gat aga att gaa atc tta tgt caa gaa aga gct tta aaa gct ttt aat       288
Asp Arg Ile Glu Ile Leu Cys Gln Glu Arg Ala Leu Lys Ala Phe Asn
                85                  90                  95 atc act tct gat aaa tgg ggg gtt aat gtt caa act ctt tct ggg tct       336
Ile Thr Ser Asp Lys Trp Gly Val Asn Val Gln Thr Leu Ser Gly Ser
            100                 105                 110 cct gct aat tta caa gtt tat caa gct att atg aaa cct cat gaa aga       384
Pro Ala Asn Leu Gln Val Tyr Gln Ala Ile Met Lys Pro His Glu Arg
        115                 120                 125 tta atg ggt ctt gat tta cct cat ggt ggt cat tta tct cat ggt tat       432
Leu Met Gly Leu Asp Leu Pro His Gly Gly His Leu Ser His Gly Tyr
    130                 135                 140 caa act gat act aga aaa atc tct gct gtt tca act tat ttt gaa act       480
Gln Thr Asp Thr Arg Lys Ile Ser Ala Val Ser Thr Tyr Phe Glu Thr
145                 150                 155                 160 atg cct tat aga gtt gat tta gaa act ggt att att gat tat gat acc       528
Met Pro Tyr Arg Val Asp Leu Glu Thr Gly Ile Ile Asp Tyr Asp Thr
```

|  |  |
|---|---:|
| tta gaa aag aat gcc tta tta ttc aga cct aag gtc ctt gtt gct ggt<br>Leu Glu Lys Asn Ala Leu Leu Phe Arg Pro Lys Val Leu Val Ala Gly<br>        180                     185                 190 | 576 |
| act tct gct tat tgt aga tta att gat tat aaa aga atg aga gaa att<br>Thr Ser Ala Tyr Cys Arg Leu Ile Asp Tyr Lys Arg Met Arg Glu Ile<br>        195                     200                 205 | 624 |
| gct gat aaa gtt ggt gct tat tta gtt gtt gat atg gct cat att tca<br>Ala Asp Lys Val Gly Ala Tyr Leu Val Val Asp Met Ala His Ile Ser<br>        210                     215                 220 | 672 |
| ggt tta atc gct gct ggt gtt atc cca tct cca ttt gaa tat gct gat<br>Gly Leu Ile Ala Ala Gly Val Ile Pro Ser Pro Phe Glu Tyr Ala Asp<br>225                   230                 235                 240 | 720 |
| att gtc act aca act aca cat aaa tcc cta aga ggt cca aga ggt gcc<br>Ile Val Thr Thr Thr Thr His Lys Ser Leu Arg Gly Pro Arg Gly Ala<br>                       245                 250                 255 | 768 |
| atg att ttc ttt aga aga ggt gtt aga tca att aac gct aaa act ggt<br>Met Ile Phe Phe Arg Arg Gly Val Arg Ser Ile Asn Ala Lys Thr Gly<br>        260                     265                 270 | 816 |
| gct gaa att aaa tat gat tta gaa aat cca att aat ttc tca gtt ttc<br>Ala Glu Ile Lys Tyr Asp Leu Glu Asn Pro Ile Asn Phe Ser Val Phe<br>        275                     280                 285 | 864 |
| cca ggt cat caa ggt ggt cca cat aat cat act att acc gcg tta gca<br>Pro Gly His Gln Gly Gly Pro His Asn His Thr Ile Thr Ala Leu Ala<br>        290                     295                 300 | 912 |
| aca gca tta aaa caa gct tca act cca gaa ttt aaa caa tat caa gaa<br>Thr Ala Leu Lys Gln Ala Ser Thr Pro Glu Phe Lys Gln Tyr Gln Glu<br>305                   310                 315                 320 | 960 |
| caa gtt tta aaa aat gct aaa gct tta gaa gaa gaa ttc tta aaa tta<br>Gln Val Leu Lys Asn Ala Lys Ala Leu Glu Glu Glu Phe Leu Lys Leu<br>                       325                 330                 335 | 1008 |
| tct tat aaa tta gtt tca aat ggt act gat tct cat atg gtt tta gtt<br>Ser Tyr Lys Leu Val Ser Asn Gly Thr Asp Ser His Met Val Leu Val<br>        340                     345                 350 | 1056 |
| tca tta aaa gat aaa ggt atc gat ggt gca aga att gaa acc gtt tgt<br>Ser Leu Lys Asp Lys Gly Ile Asp Gly Ala Arg Ile Glu Thr Val Cys<br>                       355                 360                 365 | 1104 |
| gaa aac ata aac att gcc tta aac aaa aac tca atc cca ggt gat aaa<br>Glu Asn Ile Asn Ile Ala Leu Asn Lys Asn Ser Ile Pro Gly Asp Lys<br>        370                     375                 380 | 1152 |
| tcc gct ctt gtg cca ggt ggt att aga att ggt gca cca gca atg tct<br>Ser Ala Leu Val Pro Gly Gly Ile Arg Ile Gly Ala Pro Ala Met Ser<br>385                   390                 395                 400 | 1200 |
| aca aga ggt ctt ggt gaa gaa gat ttt aaa aaa att gca cat tat att<br>Thr Arg Gly Leu Gly Glu Glu Asp Phe Lys Lys Ile Ala His Tyr Ile<br>                       405                 410                 415 | 1248 |
| gat tgg tct gtt caa tat gct aaa aaa att caa agt gaa tta cca aaa<br>Asp Trp Ser Val Gln Tyr Ala Lys Lys Ile Gln Ser Glu Leu Pro Lys<br>        420                     425                 430 | 1296 |
| gaa gct aat aga tta aaa gat ttt aaa gct aag att gct caa ggt tct<br>Glu Ala Asn Arg Leu Lys Asp Phe Lys Ala Lys Ile Ala Gln Gly Ser<br>                       435                 440                 445 | 1344 |
| gat gaa tta act aaa act aag aat gaa att tat gaa tgg gct ggt gaa<br>Asp Glu Leu Thr Lys Thr Lys Asn Glu Ile Tyr Glu Trp Ala Gly Glu<br>450                   455                 460 | 1392 |
| ttc cca tta tct gtt taa<br>Phe Pro Leu Ser Val<br>465 | 1410 |

<210> SEQ ID NO 4
<211> LENGTH: 469
<212> TYPE: PRT
<213> ORGANISM: Pichia ciferrii

<400> SEQUENCE: 4

Met Pro Tyr Ala Leu Pro Glu Ser His Arg Gln Leu Val Glu Gly His
1               5                   10                  15

Leu Lys Asp Thr Asp Pro Glu Val Glu Gln Ile Ile Lys Asp Glu Ile
            20                  25                  30

Glu Arg Gln Arg His Ser Ile Val Leu Ile Ala Ser Glu Asn Phe Thr
        35                  40                  45

Ser Thr Ala Val Phe Asp Ala Leu Gly Thr Pro Met Cys Asn Lys Tyr
    50                  55                  60

Ser Glu Gly Tyr Pro Gly Ala Arg Tyr Tyr Gly Gly Asn Glu His Ile
65                  70                  75                  80

Asp Arg Ile Glu Ile Leu Cys Gln Arg Ala Leu Lys Ala Phe Asn
                85                  90                  95

Ile Thr Ser Asp Lys Trp Gly Val Asn Val Gln Thr Leu Ser Gly Ser
            100                 105                 110

Pro Ala Asn Leu Gln Val Tyr Gln Ala Ile Met Lys Pro His Glu Arg
        115                 120                 125

Leu Met Gly Leu Asp Leu Pro His Gly His Leu Ser His Gly Tyr
    130                 135                 140

Gln Thr Asp Thr Arg Lys Ile Ser Ala Val Ser Thr Tyr Phe Glu Thr
145                 150                 155                 160

Met Pro Tyr Arg Val Asp Leu Glu Thr Gly Ile Ile Asp Tyr Asp Thr
                165                 170                 175

Leu Glu Lys Asn Ala Leu Leu Phe Arg Pro Lys Val Leu Val Ala Gly
            180                 185                 190

Thr Ser Ala Tyr Cys Arg Leu Ile Asp Tyr Lys Arg Met Arg Glu Ile
        195                 200                 205

Ala Asp Lys Val Gly Ala Tyr Leu Val Val Asp Met Ala His Ile Ser
    210                 215                 220

Gly Leu Ile Ala Ala Gly Val Ile Pro Ser Pro Phe Glu Tyr Ala Asp
225                 230                 235                 240

Ile Val Thr Thr Thr Thr His Lys Ser Leu Arg Gly Pro Arg Gly Ala
                245                 250                 255

Met Ile Phe Phe Arg Arg Gly Val Arg Ser Ile Asn Ala Lys Thr Gly
            260                 265                 270

Ala Glu Ile Lys Tyr Asp Leu Glu Asn Pro Ile Asn Phe Ser Val Phe
        275                 280                 285

Pro Gly His Gln Gly Gly Pro His Asn His Thr Ile Thr Ala Leu Ala
    290                 295                 300

Thr Ala Leu Lys Gln Ala Ser Thr Pro Glu Phe Lys Gln Tyr Gln Glu
305                 310                 315                 320

Gln Val Leu Lys Asn Ala Lys Ala Leu Glu Glu Phe Leu Lys Leu
                325                 330                 335

Ser Tyr Lys Leu Val Ser Asn Gly Thr Asp Ser His Met Val Leu Val
            340                 345                 350

Ser Leu Lys Asp Lys Gly Ile Asp Gly Ala Arg Ile Glu Thr Val Cys
        355                 360                 365

Glu Asn Ile Asn Ile Ala Leu Asn Lys Asn Ser Ile Pro Gly Asp Lys
    370                 375                 380

```
Ser Ala Leu Val Pro Gly Gly Ile Arg Ile Gly Ala Pro Ala Met Ser
385                 390                 395                 400

Thr Arg Gly Leu Gly Glu Glu Asp Phe Lys Lys Ile Ala His Tyr Ile
            405                 410                 415

Asp Trp Ser Val Gln Tyr Ala Lys Lys Ile Gln Ser Glu Leu Pro Lys
        420                 425                 430

Glu Ala Asn Arg Leu Lys Asp Phe Lys Ala Lys Ile Ala Gln Gly Ser
    435                 440                 445

Asp Glu Leu Thr Lys Thr Lys Asn Glu Ile Tyr Glu Trp Ala Gly Glu
        450                 455                 460

Phe Pro Leu Ser Val
465

<210> SEQ ID NO 5
<211> LENGTH: 1029
<212> TYPE: DNA
<213> ORGANISM: Pichia ciferrii
<220> FEATURE:
<221> NAME/KEY: CDS
<222> LOCATION: (1)..(1029)

<400> SEQUENCE: 5 atg aca atc aca aaa gat cat aaa gtc cca tac atc aag act cca tta      48
Met Thr Ile Thr Lys Asp His Lys Val Pro Tyr Ile Lys Thr Pro Leu
1               5                   10                  15 gtt gat tgt aaa gaa cta tca gaa caa tca cca tgt aga ata ttc cta      96
Val Asp Cys Lys Glu Leu Ser Glu Gln Ser Pro Cys Arg Ile Phe Leu
                20                  25                  30 aag caa gaa ttc att caa cca tcg ggt tct tac aaa ata cgt gga ctt     144
Lys Gln Glu Phe Ile Gln Pro Ser Gly Ser Tyr Lys Ile Arg Gly Leu
            35                  40                  45 tca aat tta att aga act tca att gaa gaa att aaa tca aat cct aat     192
Ser Asn Leu Ile Arg Thr Ser Ile Glu Glu Ile Lys Ser Asn Pro Asn
        50                  55                  60 aat ttg ggt aaa aca att cat gtt tat gct gct tct ggt ggt aat gct     240
Asn Leu Gly Lys Thr Ile His Val Tyr Ala Ala Ser Gly Gly Asn Ala
65                  70                  75                  80 ggt aat gct gtc tct tgt gct tct caa ttt tat gga tta gaa tca aca     288
Gly Asn Ala Val Ser Cys Ala Ser Gln Phe Tyr Gly Leu Glu Ser Thr
                85                  90                  95 gtt gtt ata cca aaa gct aca agt gat aaa atg aag caa aaa atc ttt     336
Val Val Ile Pro Lys Ala Thr Ser Asp Lys Met Lys Gln Lys Ile Phe
                100                 105                 110 aaa aat gga tca aaa ata att gtt caa ggt gaa act att ggt gaa gct     384
Lys Asn Gly Ser Lys Ile Ile Val Gln Gly Glu Thr Ile Gly Glu Ala
            115                 120                 125 gca att tat tta aaa gat gtc tta atc cct tca tta gat gat tct att     432
Ala Ile Tyr Leu Lys Asp Val Leu Ile Pro Ser Leu Asp Asp Ser Ile
        130                 135                 140 ata cct atc tat tgt cat cct tat gat atc cca gct ata tgg cat ggt     480
Ile Pro Ile Tyr Cys His Pro Tyr Asp Ile Pro Ala Ile Trp His Gly
145                 150                 155                 160 cat tct tct att ata gat gaa att gtt gat caa ttg gcc tct tca aat     528
His Ser Ser Ile Ile Asp Glu Ile Val Asp Gln Leu Ala Ser Ser Asn
                165                 170                 175 gaa tta tca aaa tta aaa ggt att gtt tgt tca att ggt ggt ggt gga     576
Glu Leu Ser Lys Leu Lys Gly Ile Val Cys Ser Ile Gly Gly Gly Gly
            180                 185                 190 ctt tat aat ggt tta gtt caa ggt tta caa aga aat caa tta tca aaa     624
Leu Tyr Asn Gly Leu Val Gln Gly Leu Gln Arg Asn Gln Leu Ser Lys
```

```
                 195                 200                 205
att cca ata atg act tta gaa aca gat act tgt cca act ttc cat gaa       672
Ile Pro Ile Met Thr Leu Glu Thr Asp Thr Cys Pro Thr Phe His Glu
    210                 215                 220 tct att aaa gca caa aaa caa gta ttc att aaa aaa acc aat aca att       720
Ser Ile Lys Ala Gln Lys Gln Val Phe Ile Lys Lys Thr Asn Thr Ile
225                 230                 235                 240 gca att tct tta gct tgt cct tat gtc tct ttg aaa act ctt gaa tat       768
Ala Ile Ser Leu Ala Cys Pro Tyr Val Ser Leu Lys Thr Leu Glu Tyr
                245                 250                 255 tat aat tct cac aag act aag aat tta tta gtt agt gat tct gat gct       816
Tyr Asn Ser His Lys Thr Lys Asn Leu Leu Val Ser Asp Ser Asp Ala
            260                 265                 270 gca aat tct tgt tta aat ttt gca aat gaa ttt aat att ata gtg gaa       864
Ala Asn Ser Cys Leu Asn Phe Ala Asn Glu Phe Asn Ile Ile Val Glu
        275                 280                 285 cct gct tgt gga gtt gct ttg tgc agt gtt tat aat aat ttg att caa       912
Pro Ala Cys Gly Val Ala Leu Cys Ser Val Tyr Asn Asn Leu Ile Gln
    290                 295                 300 aaa aat att gaa ttt ttt gat gat tta aaa tct gat gat att gtg gtt       960
Lys Asn Ile Glu Phe Phe Asp Asp Leu Lys Ser Asp Asp Ile Val Val
305                 310                 315                 320 att att gtt tgt ggt ggg agt tca aca acc gtt caa gat tta aca aat      1008
Ile Ile Val Cys Gly Gly Ser Ser Thr Thr Val Gln Asp Leu Thr Asn
                325                 330                 335 tat aaa cta ctc tat cat tag                                           1029
Tyr Lys Leu Leu Tyr His
            340

<210> SEQ ID NO 6
<211> LENGTH: 342
<212> TYPE: PRT
<213> ORGANISM: Pichia ciferrii

<400> SEQUENCE: 6

Met Thr Ile Thr Lys Asp His Lys Val Pro Tyr Ile Lys Thr Pro Leu
1               5                   10                  15

Val Asp Cys Lys Glu Leu Ser Glu Gln Ser Pro Cys Arg Ile Phe Leu
            20                  25                  30

Lys Gln Glu Phe Ile Gln Pro Ser Gly Ser Tyr Lys Ile Arg Gly Leu
        35                  40                  45

Ser Asn Leu Ile Arg Thr Ser Ile Glu Glu Ile Lys Ser Asn Pro Asn
    50                  55                  60

Asn Leu Gly Lys Thr Ile His Val Tyr Ala Ala Ser Gly Gly Asn Ala
65                  70                  75                  80

Gly Asn Ala Val Ser Cys Ala Ser Gln Phe Tyr Gly Leu Glu Ser Thr
            85                  90                  95

Val Val Ile Pro Lys Ala Thr Ser Asp Lys Met Lys Gln Lys Ile Phe
        100                 105                 110

Lys Asn Gly Ser Lys Ile Ile Val Gln Gly Glu Thr Ile Gly Glu Ala
    115                 120                 125

Ala Ile Tyr Leu Lys Asp Val Leu Ile Pro Ser Leu Asp Asp Ser Ile
130                 135                 140

Ile Pro Ile Tyr Cys His Pro Tyr Asp Ile Pro Ala Ile Trp His Gly
145                 150                 155                 160

His Ser Ser Ile Ile Asp Glu Ile Val Asp Gln Leu Ala Ser Ser Asn
            165                 170                 175
```

```
Glu Leu Ser Lys Leu Lys Gly Ile Val Cys Ser Ile Gly Gly Gly
            180                 185                 190

Leu Tyr Asn Gly Leu Val Gln Gly Leu Gln Arg Asn Gln Leu Ser Lys
            195                 200                 205

Ile Pro Ile Met Thr Leu Glu Thr Asp Thr Cys Pro Thr Phe His Glu
    210                 215                 220

Ser Ile Lys Ala Gln Lys Gln Val Phe Ile Lys Lys Thr Asn Thr Ile
225                 230                 235                 240

Ala Ile Ser Leu Ala Cys Pro Tyr Val Ser Leu Lys Thr Leu Glu Tyr
                245                 250                 255

Tyr Asn Ser His Lys Thr Lys Asn Leu Leu Val Ser Asp Ser Asp Ala
            260                 265                 270

Ala Asn Ser Cys Leu Asn Phe Ala Asn Glu Phe Asn Ile Ile Val Glu
        275                 280                 285

Pro Ala Cys Gly Val Ala Leu Cys Ser Val Tyr Asn Asn Leu Ile Gln
    290                 295                 300

Lys Asn Ile Glu Phe Phe Asp Asp Leu Lys Ser Asp Ile Val Val
305                 310                 315                 320

Ile Ile Val Cys Gly Gly Ser Ser Thr Val Gln Asp Leu Thr Asn
                325                 330                 335

Tyr Lys Leu Leu Tyr His
            340

<210> SEQ ID NO 7
<211> LENGTH: 1530
<212> TYPE: DNA
<213> ORGANISM: Pichia ciferrii
<220> FEATURE:
<221> NAME/KEY: CDS
<222> LOCATION: (1)..(1530)

<400> SEQUENCE: 7 atg ccg agt ttt gac tct caa aga att aaa ctg atg gat aca gta tca      48
Met Pro Ser Phe Asp Ser Gln Arg Ile Lys Leu Met Asp Thr Val Ser
1               5                   10                  15 gta aac ccc cca aga gcc atc att ggt gat aca ggt atc atc att aaa      96
Val Asn Pro Pro Arg Ala Ile Ile Gly Asp Thr Gly Ile Ile Ile Lys
            20                  25                  30 gat caa tct tca ttc tat tac aat caa cat gat aac gct tca ttt tca     144
Asp Gln Ser Ser Phe Tyr Tyr Asn Gln His Asp Asn Ala Ser Phe Ser
        35                  40                  45 tct tgc tta agt tgc tct tca tca aac tcg aat ggt acg gtg aaa tct     192
Ser Cys Leu Ser Cys Ser Ser Ser Asn Ser Asn Gly Thr Val Lys Ser
    50                  55                  60 tca ggt cca aaa cat att cca ttt gtt gat ata ttg agt gtt cga tat     240
Ser Gly Pro Lys His Ile Pro Phe Val Asp Ile Leu Ser Val Arg Tyr
65                  70                  75                  80 ata aat gaa aat aat gaa tct tta tta gaa gct gga agt tcc act gtg     288
Ile Asn Glu Asn Asn Glu Ser Leu Leu Glu Ala Gly Ser Ser Thr Val
                85                  90                  95 act agt gat gaa cct gat gtc gaa gtg gta ttt gtt aga caa aag ggt     336
Thr Ser Asp Glu Pro Asp Val Glu Val Val Phe Val Arg Gln Lys Gly
            100                 105                 110 aaa act ctt gta cca act cca ata ata tta tca ata gat act tta ggt     384
Lys Thr Leu Val Pro Thr Pro Ile Ile Leu Ser Ile Asp Thr Leu Gly
        115                 120                 125 cat gat gat gtt gta caa gaa att tgg aga tta agt tat caa gga aca     432
His Asp Asp Val Val Gln Glu Ile Trp Arg Leu Ser Tyr Gln Gly Thr
    130                 135                 140
```

| | | | | | | | | | | | | | | | | |
|---|---|---|---|---|---|---|---|---|---|---|---|---|---|---|---|---|
| aaa | cca | aga | aaa | tca | ata | tta | gtt | ctt | gtt | aat | cca | cat | ggt | ggg | aaa | 480 |
| Lys | Pro | Arg | Lys | Ser | Ile | Leu | Val | Leu | Val | Asn | Pro | His | Gly | Gly | Lys | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| ggt | aaa | gct | ata | aat | tca | ttc | tta | act | caa | tca | aaa | cct | gta | tta | att | 528 |
| Gly | Lys | Ala | Ile | Asn | Ser | Phe | Leu | Thr | Gln | Ser | Lys | Pro | Val | Leu | Ile | |
| | | | | 165 | | | | | 170 | | | | | 175 | | |

| | | | | | | | | | | | | | | | | |
|---|---|---|---|---|---|---|---|---|---|---|---|---|---|---|---|---|
| ggt | gct | caa | gct | tct | gtt | gaa | gtt | aga | cat | act | caa | tat | tat | caa | cat | 576 |
| Gly | Ala | Gln | Ala | Ser | Val | Glu | Val | Arg | His | Thr | Gln | Tyr | Tyr | Gln | His | |
| | | | 180 | | | | | 185 | | | | | 190 | | | |

| | | | | | | | | | | | | | | | | |
|---|---|---|---|---|---|---|---|---|---|---|---|---|---|---|---|---|
| gct | aca | gat | att | gca | cgc | act | ttg | aat | att | gat | aaa | tat | gat | ata | att | 624 |
| Ala | Thr | Asp | Ile | Ala | Arg | Thr | Leu | Asn | Ile | Asp | Lys | Tyr | Asp | Ile | Ile | |
| | | | | 195 | | | | | 200 | | | | | 205 | | |

| | | | | | | | | | | | | | | | | |
|---|---|---|---|---|---|---|---|---|---|---|---|---|---|---|---|---|
| gca | tgt | gct | tca | ggt | gat | ggt | gtc | cca | cat | gaa | gtc | ttg | aat | gga | ttt | 672 |
| Ala | Cys | Ala | Ser | Gly | Asp | Gly | Val | Pro | His | Glu | Val | Leu | Asn | Gly | Phe | |
| 210 | | | | | 215 | | | | | 220 | | | | | | |

| | | | | | | | | | | | | | | | | |
|---|---|---|---|---|---|---|---|---|---|---|---|---|---|---|---|---|
| tat | caa | aga | tct | gat | aga | gct | gaa | gct | ttc | aat | aag | att | aca | ata | act | 720 |
| Tyr | Gln | Arg | Ser | Asp | Arg | Ala | Glu | Ala | Phe | Asn | Lys | Ile | Thr | Ile | Thr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| caa | tta | cca | tgt | ggt | tca | ggt | aat | gca | atg | agt | gaa | tca | tgt | cat | ggt | 768 |
| Gln | Leu | Pro | Cys | Gly | Ser | Gly | Asn | Ala | Met | Ser | Glu | Ser | Cys | His | Gly | |
| | | | | 245 | | | | | 250 | | | | | 255 | | |

| | | | | | | | | | | | | | | | | |
|---|---|---|---|---|---|---|---|---|---|---|---|---|---|---|---|---|
| aca | aat | aat | cca | agt | ttt | gcc | gct | cta | tca | tta | ttg | aaa | tca | agt | acg | 816 |
| Thr | Asn | Asn | Pro | Ser | Phe | Ala | Ala | Leu | Ser | Leu | Leu | Lys | Ser | Ser | Thr | |
| | | | 260 | | | | | 265 | | | | | 270 | | | |

| | | | | | | | | | | | | | | | | |
|---|---|---|---|---|---|---|---|---|---|---|---|---|---|---|---|---|
| gta | aat | tta | gat | tta | atg | gct | tgt | aca | caa | ggt | gat | aaa | act | tat | gtt | 864 |
| Val | Asn | Leu | Asp | Leu | Met | Ala | Cys | Thr | Gln | Gly | Asp | Lys | Thr | Tyr | Val | |
| | | 275 | | | | | 280 | | | | | 285 | | | | |

| | | | | | | | | | | | | | | | | |
|---|---|---|---|---|---|---|---|---|---|---|---|---|---|---|---|---|
| tca | ttc | tta | agt | caa | act | gtc | ggt | gtt | ata | gca | gat | tct | gat | att | ggt | 912 |
| Ser | Phe | Leu | Ser | Gln | Thr | Val | Gly | Val | Ile | Ala | Asp | Ser | Asp | Ile | Gly | |
| | | 290 | | | | | 295 | | | | | 300 | | | | |

| | | | | | | | | | | | | | | | | |
|---|---|---|---|---|---|---|---|---|---|---|---|---|---|---|---|---|
| act | gaa | gca | ctt | aga | tgg | tta | ggt | cct | tca | aga | ttt | gaa | tta | ggt | gtt | 960 |
| Thr | Glu | Ala | Leu | Arg | Trp | Leu | Gly | Pro | Ser | Arg | Phe | Glu | Leu | Gly | Val | |
| 305 | | | | 310 | | | | | 315 | | | | | 320 | | |

| | | | | | | | | | | | | | | | | |
|---|---|---|---|---|---|---|---|---|---|---|---|---|---|---|---|---|
| gct | tat | aaa | gtt | tta | tca | aga | tca | aga | tat | cca | tgt | gat | ata | tct | gtt | 1008 |
| Ala | Tyr | Lys | Val | Leu | Ser | Arg | Ser | Arg | Tyr | Pro | Cys | Asp | Ile | Ser | Val | |
| | | | | 325 | | | | | 330 | | | | | 335 | | |

| | | | | | | | | | | | | | | | | |
|---|---|---|---|---|---|---|---|---|---|---|---|---|---|---|---|---|
| aaa | tat | gct | gca | aaa | tcg | aaa | aat | gaa | tta | aga | caa | cat | ttt | gat | gaa | 1056 |
| Lys | Tyr | Ala | Ala | Lys | Ser | Lys | Asn | Glu | Leu | Arg | Gln | His | Phe | Asp | Glu | |
| | | | 340 | | | | | 345 | | | | | 350 | | | |

| | | | | | | | | | | | | | | | | |
|---|---|---|---|---|---|---|---|---|---|---|---|---|---|---|---|---|
| cat | tcc | act | att | gtt | tca | aca | aaa | gat | atc | caa | ata | act | gaa | gat | act | 1104 |
| His | Ser | Thr | Ile | Val | Ser | Thr | Lys | Asp | Ile | Gln | Ile | Thr | Glu | Asp | Thr | |
| | | | 355 | | | | | 360 | | | | | 365 | | | |

| | | | | | | | | | | | | | | | | |
|---|---|---|---|---|---|---|---|---|---|---|---|---|---|---|---|---|
| tat | aat | tta | aaa | tat | gat | cca | aat | ggt | cca | ata | cct | gat | gat | tgg | gaa | 1152 |
| Tyr | Asn | Leu | Lys | Tyr | Asp | Pro | Asn | Gly | Pro | Ile | Pro | Asp | Asp | Trp | Glu | |
| | 370 | | | | | 375 | | | | | 380 | | | | | |

| | | | | | | | | | | | | | | | | |
|---|---|---|---|---|---|---|---|---|---|---|---|---|---|---|---|---|
| gag | att | gat | aaa | gat | ctt | tca | gaa | aat | tta | ggt | att | ttc | tat | aca | ggt | 1200 |
| Glu | Ile | Asp | Lys | Asp | Leu | Ser | Glu | Asn | Leu | Gly | Ile | Phe | Tyr | Thr | Gly | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| aaa | atg | cca | tat | att | gca | aaa | gat | gtt | caa | ttt | ttc | cct | gca | gct | tta | 1248 |
| Lys | Met | Pro | Tyr | Ile | Ala | Lys | Asp | Val | Gln | Phe | Phe | Pro | Ala | Ala | Leu | |
| | | | | 405 | | | | | 410 | | | | | 415 | | |

| | | | | | | | | | | | | | | | | |
|---|---|---|---|---|---|---|---|---|---|---|---|---|---|---|---|---|
| cca | aat | gat | ggt | act | ttt | gat | tta | gtt | ata | aca | gat | gct | cgt | aca | agt | 1296 |
| Pro | Asn | Asp | Gly | Thr | Phe | Asp | Leu | Val | Ile | Thr | Asp | Ala | Arg | Thr | Ser | |
| | | | 420 | | | | | 425 | | | | | 430 | | | |

| | | | | | | | | | | | | | | | | |
|---|---|---|---|---|---|---|---|---|---|---|---|---|---|---|---|---|
| ata | gca | cgt | atg | gca | cca | act | tta | tta | tca | tta | gat | caa | ggt | tct | cat | 1344 |
| Ile | Ala | Arg | Met | Ala | Pro | Thr | Leu | Leu | Ser | Leu | Asp | Gln | Gly | Ser | His | |
| | | 435 | | | | | 440 | | | | | 445 | | | | |

| | | | | | | | | | | | | | | | | |
|---|---|---|---|---|---|---|---|---|---|---|---|---|---|---|---|---|
| gtt | tta | caa | cca | gaa | gtt | caa | cat | tct | aaa | ata | ata | gca | tat | aga | tta | 1392 |
| Val | Leu | Gln | Pro | Glu | Val | Gln | His | Ser | Lys | Ile | Ile | Ala | Tyr | Arg | Leu | |

```
                  450            455             460
act cca aag cag caa cat ggt tat tta agt gtt gat ggt gaa agt tat    1440
Thr Pro Lys Gln Gln His Gly Tyr Leu Ser Val Asp Gly Glu Ser Tyr
465                 470                 475                 480 cca ttt gaa act att caa gtt gaa att cta ccc ggt gct gca aag act    1488
Pro Phe Glu Thr Ile Gln Val Glu Ile Leu Pro Gly Ala Ala Lys Thr
                485                 490                 495 tta cta aga aat ggt act tat gtt gaa aca aat ttt tat tga            1530
Leu Leu Arg Asn Gly Thr Tyr Val Glu Thr Asn Phe Tyr
                500                 505

<210> SEQ ID NO 8
<211> LENGTH: 509
<212> TYPE: PRT
<213> ORGANISM: Pichia ciferrii

<400> SEQUENCE: 8

Met Pro Ser Phe Asp Ser Gln Arg Ile Lys Leu Met Asp Thr Val Ser
1               5                   10                  15

Val Asn Pro Pro Arg Ala Ile Ile Gly Asp Thr Gly Ile Ile Ile Lys
            20                  25                  30

Asp Gln Ser Ser Phe Tyr Tyr Asn Gln His Asp Asn Ala Ser Phe Ser
        35                  40                  45

Ser Cys Leu Ser Cys Ser Ser Ser Asn Ser Asn Gly Thr Val Lys Ser
    50                  55                  60

Ser Gly Pro Lys His Ile Pro Phe Val Asp Ile Leu Ser Val Arg Tyr
65                  70                  75                  80

Ile Asn Glu Asn Asn Glu Ser Leu Leu Glu Ala Gly Ser Ser Thr Val
                85                  90                  95

Thr Ser Asp Glu Pro Asp Val Glu Val Val Phe Val Arg Gln Lys Gly
            100                 105                 110

Lys Thr Leu Val Pro Thr Pro Ile Ile Leu Ser Ile Asp Thr Leu Gly
        115                 120                 125

His Asp Asp Val Val Gln Glu Ile Trp Arg Leu Ser Tyr Gln Gly Thr
    130                 135                 140

Lys Pro Arg Lys Ser Ile Leu Val Leu Val Asn Pro His Gly Gly Lys
145                 150                 155                 160

Gly Lys Ala Ile Asn Ser Phe Leu Thr Gln Ser Lys Pro Val Leu Ile
                165                 170                 175

Gly Ala Gln Ala Ser Val Glu Val Arg His Thr Gln Tyr Tyr Gln His
            180                 185                 190

Ala Thr Asp Ile Ala Arg Thr Leu Asn Ile Asp Lys Tyr Asp Ile Ile
        195                 200                 205

Ala Cys Ala Ser Gly Asp Gly Val Pro His Glu Val Leu Asn Gly Phe
    210                 215                 220

Tyr Gln Arg Ser Asp Arg Ala Glu Ala Phe Asn Lys Ile Thr Ile Thr
225                 230                 235                 240

Gln Leu Pro Cys Gly Ser Gly Asn Ala Met Ser Glu Ser Cys His Gly
                245                 250                 255

Thr Asn Asn Pro Ser Phe Ala Ala Leu Ser Leu Leu Lys Ser Ser Thr
            260                 265                 270

Val Asn Leu Asp Leu Met Ala Cys Thr Gln Gly Asp Lys Thr Tyr Val
        275                 280                 285

Ser Phe Leu Ser Gln Thr Val Gly Val Ile Ala Asp Ser Asp Ile Gly
    290                 295                 300
```

```
Thr Glu Ala Leu Arg Trp Leu Gly Pro Ser Arg Phe Glu Leu Gly Val
305                 310                 315                 320

Ala Tyr Lys Val Leu Ser Arg Ser Arg Tyr Pro Cys Asp Ile Ser Val
                325                 330                 335

Lys Tyr Ala Ala Lys Ser Lys Asn Glu Leu Arg Gln His Phe Asp Glu
            340                 345                 350

His Ser Thr Ile Val Ser Thr Lys Asp Ile Gln Ile Thr Glu Asp Thr
        355                 360                 365

Tyr Asn Leu Lys Tyr Asp Pro Asn Gly Pro Ile Pro Asp Asp Trp Glu
370                 375                 380

Glu Ile Asp Lys Asp Leu Ser Glu Asn Leu Gly Ile Phe Tyr Thr Gly
385                 390                 395                 400

Lys Met Pro Tyr Ile Ala Lys Asp Val Gln Phe Phe Pro Ala Ala Leu
                405                 410                 415

Pro Asn Asp Gly Thr Phe Asp Leu Val Ile Thr Asp Ala Arg Thr Ser
            420                 425                 430

Ile Ala Arg Met Ala Pro Thr Leu Leu Ser Leu Asp Gln Gly Ser His
        435                 440                 445

Val Leu Gln Pro Glu Val Gln His Ser Lys Ile Ile Ala Tyr Arg Leu
450                 455                 460

Thr Pro Lys Gln Gln His Gly Tyr Leu Ser Val Asp Gly Glu Ser Tyr
465                 470                 475                 480

Pro Phe Glu Thr Ile Gln Val Glu Ile Leu Pro Gly Ala Ala Lys Thr
                485                 490                 495

Leu Leu Arg Asn Gly Thr Tyr Val Glu Thr Asn Phe Tyr
            500                 505

<210> SEQ ID NO 9
<211> LENGTH: 1515
<212> TYPE: DNA
<213> ORGANISM: Pichia ciferrii
<220> FEATURE:
<221> NAME/KEY: CDS
<222> LOCATION: (1)..(1515)

<400> SEQUENCE: 9 ttg gcg gtt aac atc act ggt tat ggg tta atc ggc tac tta aag atc      48
Met Ala Val Asn Ile Thr Gly Tyr Gly Leu Ile Gly Tyr Leu Lys Ile
1               5                   10                  15 gta tat aat gaa tta gca aaa gct gta ttc aga aca ttt tta tcc tta      96
Val Tyr Asn Glu Leu Ala Lys Ala Val Phe Arg Thr Phe Leu Ser Leu
            20                  25                  30 cca ttt gtt aaa agt aaa gtt gat tca gaa gtt aga gaa aat ttg gac     144
Pro Phe Val Lys Ser Lys Val Asp Ser Glu Val Arg Glu Asn Leu Asp
        35                  40                  45 aaa tta gaa gat tct tta att gtc aaa aca cca aat gtt caa gat ttc     192
Lys Leu Glu Asp Ser Leu Ile Val Lys Thr Pro Asn Val Gln Asp Phe
    50                  55                  60 caa tca ata cca aca act ggt tta tca gat gat agc att tta gac tta     240
Gln Ser Ile Pro Thr Thr Gly Leu Ser Asp Asp Ser Ile Leu Asp Leu
65                  70                  75                  80 ttg caa aaa cta caa aat tta aaa cat tca gat tgg caa ggt ggt aaa     288
Leu Gln Lys Leu Gln Asn Leu Lys His Ser Asp Trp Gln Gly Gly Lys
                85                  90                  95 gtc tca ggt gct gtt tac cat ggt ggt gat gat att att aag atc caa     336
Val Ser Gly Ala Val Tyr His Gly Gly Asp Asp Ile Ile Lys Ile Gln
            100                 105                 110 tct gat gct ttc aaa gtc ttt tgt gtt gct aat caa tta cat cca gac     384
```

```
Ser Asp Ala Phe Lys Val Phe Cys Val Ala Asn Gln Leu His Pro Asp
        115                 120                 125 gtt ttc cca ggt gtt cgt aaa atg gaa gct gaa gtt gtt gca atg act    432
Val Phe Pro Gly Val Arg Lys Met Glu Ala Glu Val Val Ala Met Thr
        130                 135                 140 ttg aaa tta ttc aat gca cca gaa tca ggt gtt ggt ggt acc agc tca    480
Leu Lys Leu Phe Asn Ala Pro Glu Ser Gly Val Gly Gly Thr Ser Ser
145                 150                 155                 160 ggt ggt act gaa tcc tta tta ttg gct tgt ctt tct gct aaa gaa tat    528
Gly Gly Thr Glu Ser Leu Leu Leu Ala Cys Leu Ser Ala Lys Glu Tyr
                    165                 170                 175 ggt aaa cgt cat aaa ggt att gtt gaa cca gaa att att att cca gaa    576
Gly Lys Arg His Lys Gly Ile Val Glu Pro Glu Ile Ile Ile Pro Glu
                180                 185                 190 act gca cat gct ggt ttt gat aaa gct ggt tat tat ttt ggt atg aaa    624
Thr Ala His Ala Gly Phe Asp Lys Ala Gly Tyr Tyr Phe Gly Met Lys
            195                 200                 205 gtc cat cat gtt cca tta gat cca aag acc tat aaa gtt gat tta ggg    672
Val His His Val Pro Leu Asp Pro Lys Thr Tyr Lys Val Asp Leu Gly
        210                 215                 220 aaa tta aag aga tta atc aat aaa aac act gtt tta tta gct ggt tct    720
Lys Leu Lys Arg Leu Ile Asn Lys Asn Thr Val Leu Leu Ala Gly Ser
225                 230                 235                 240 gca cca aat ttc cca cat ggt atc att gat gat att gaa tct att ggt    768
Ala Pro Asn Phe Pro His Gly Ile Ile Asp Asp Ile Glu Ser Ile Gly
                    245                 250                 255 gct cta ggt caa aaa tat aat atc cca gtt cat gtt gat tgt tgt tta    816
Ala Leu Gly Gln Lys Tyr Asn Ile Pro Val His Val Asp Cys Cys Leu
                260                 265                 270 ggt tca ttt att gtc tct tat atg gaa aaa gca ggt tat gaa tta cca    864
Gly Ser Phe Ile Val Ser Tyr Met Glu Lys Ala Gly Tyr Glu Leu Pro
            275                 280                 285 cct ttt gac ttt aga gtt cct ggt gtc act tca att tct tgt gat acc    912
Pro Phe Asp Phe Arg Val Pro Gly Val Thr Ser Ile Ser Cys Asp Thr
        290                 295                 300 cac aaa tac ggg ttt gca cca aaa ggt tct tca ata atc atg tat cgt    960
His Lys Tyr Gly Phe Ala Pro Lys Gly Ser Ser Ile Ile Met Tyr Arg
305                 310                 315                 320 aat aat gct ctt aga gaa gca caa tat tat gtt aat gtt gac tgg gtt   1008
Asn Asn Ala Leu Arg Glu Ala Gln Tyr Tyr Val Asn Val Asp Trp Val
                    325                 330                 335 ggt ggt atc tat ggc tca cca act tta gct ggt agt aga cca ggt gct   1056
Gly Gly Ile Tyr Gly Ser Pro Thr Leu Ala Gly Ser Arg Pro Gly Ala
                340                 345                 350 atc att gtt ggt tgt tgg gca acc ttg atc aag att ggt gat gaa ggt   1104
Ile Ile Val Gly Cys Trp Ala Thr Leu Ile Lys Ile Gly Asp Glu Gly
            355                 360                 365 tac aag aaa tca tgt aaa gat att gtt gga gct gca aga aaa ttg aaa   1152
Tyr Lys Lys Ser Cys Lys Asp Ile Val Gly Ala Ala Arg Lys Leu Lys
        370                 375                 380 tta aga att caa aaa gaa ata cca gaa tta gaa atc att ggt gat cca   1200
Leu Arg Ile Gln Lys Glu Ile Pro Glu Leu Glu Ile Ile Gly Asp Pro
385                 390                 395                 400 tta act tca gtt att tca ttc aaa tct gaa aaa att aat att tat gaa   1248
Leu Thr Ser Val Ile Ser Phe Lys Ser Glu Lys Ile Asn Ile Tyr Glu
                    405                 410                 415 tta tca gat ctc ttg agt tct aag gga tgg cac tta agt gca ttg caa   1296
Leu Ser Asp Leu Leu Ser Ser Lys Gly Trp His Leu Ser Ala Leu Gln
                420                 425                 430
```

| | | | | | | | | | | | | | | |
|---|---|---|---|---|---|---|---|---|---|---|---|---|---|---|
| aag | cca | gca | gct | tta | cat | ctt | gca | gtc | act | aga | tta | tca | gtt | cca | gtt | 1344 |
| Lys | Pro | Ala | Ala | Leu | His | Leu | Ala | Val | Thr | Arg | Leu | Ser | Val | Pro | Val | |
| | | 435 | | | | 440 | | | | | 445 | | | | | |
| att | gat | gaa | tta | gtt | gat | gaa | ttg | aaa | aca | gct | gtt | cac | aaa | ttg | aga | 1392 |
| Ile | Asp | Glu | Leu | Val | Asp | Glu | Leu | Lys | Thr | Ala | Val | His | Lys | Leu | Arg | |
| | 450 | | | | | 455 | | | | | 460 | | | | | |
| gat | tca | tct | gct | gct | aaa | ggt | gat | act | gct | gca | tta | tac | ggt | gtc | gct | 1440 |
| Asp | Ser | Ser | Ala | Ala | Lys | Gly | Asp | Thr | Ala | Ala | Leu | Tyr | Gly | Val | Ala | |
| 465 | | | | | 470 | | | | | 475 | | | | | 480 | |
| ggt | agt | gtt | tcc | acc | act | ggt | gtt | gtt | gat | cgt | tta | gtt | gtt | gga | ttc | 1488 |
| Gly | Ser | Val | Ser | Thr | Thr | Gly | Val | Val | Asp | Arg | Leu | Val | Val | Gly | Phe | |
| | | | | 485 | | | | | 490 | | | | | 495 | | |
| tta | gat | aca | cta | tac | aaa | acc | aaa | taa | | | | | | | | 1515 |
| Leu | Asp | Thr | Leu | Tyr | Lys | Thr | Lys | | | | | | | | | |
| | | | | 500 | | | | | | | | | | | | |

<210> SEQ ID NO 10
<211> LENGTH: 504
<212> TYPE: PRT
<213> ORGANISM: Pichia ciferrii

<400> SEQUENCE: 10

Met Ala Val Asn Ile Thr Gly Tyr Gly Leu Ile Gly Tyr Leu Lys Ile
1               5                   10                  15

Val Tyr Asn Glu Leu Ala Lys Ala Val Phe Arg Thr Phe Leu Ser Leu
            20                  25                  30

Pro Phe Val Lys Ser Lys Val Asp Ser Glu Val Arg Glu Asn Leu Asp
        35                  40                  45

Lys Leu Glu Asp Ser Leu Ile Val Lys Thr Pro Asn Val Gln Asp Phe
    50                  55                  60

Gln Ser Ile Pro Thr Thr Gly Leu Ser Asp Asp Ser Ile Leu Asp Leu
65                  70                  75                  80

Leu Gln Lys Leu Gln Asn Leu Lys His Ser Asp Trp Gln Gly Gly Lys
                85                  90                  95

Val Ser Gly Ala Val Tyr His Gly Gly Asp Ile Ile Lys Ile Gln
            100                 105                 110

Ser Asp Ala Phe Lys Val Phe Cys Val Ala Asn Gln Leu His Pro Asp
        115                 120                 125

Val Phe Pro Gly Val Arg Lys Met Glu Ala Glu Val Val Ala Met Thr
    130                 135                 140

Leu Lys Leu Phe Asn Ala Pro Glu Ser Gly Val Gly Gly Thr Ser Ser
145                 150                 155                 160

Gly Gly Thr Glu Ser Leu Leu Leu Ala Cys Leu Ser Ala Lys Glu Tyr
                165                 170                 175

Gly Lys Arg His Lys Gly Ile Val Glu Pro Glu Ile Ile Pro Glu
            180                 185                 190

Thr Ala His Ala Gly Phe Asp Lys Ala Gly Tyr Tyr Phe Gly Met Lys
        195                 200                 205

Val His His Val Pro Leu Asp Pro Lys Thr Tyr Lys Val Asp Leu Gly
    210                 215                 220

Lys Leu Lys Arg Leu Ile Asn Lys Asn Thr Val Leu Leu Ala Gly Ser
225                 230                 235                 240

Ala Pro Asn Phe Pro His Gly Ile Ile Asp Asp Ile Glu Ser Ile Gly
                245                 250                 255

Ala Leu Gly Gln Lys Tyr Asn Ile Pro Val His Val Asp Cys Cys Leu
            260                 265                 270

```
Gly Ser Phe Ile Val Ser Tyr Met Glu Lys Ala Gly Tyr Glu Leu Pro
            275                 280                 285

Pro Phe Asp Phe Arg Val Pro Gly Val Thr Ser Ile Ser Cys Asp Thr
        290                 295                 300

His Lys Tyr Gly Phe Ala Pro Lys Gly Ser Ser Ile Ile Met Tyr Arg
305                 310                 315                 320

Asn Asn Ala Leu Arg Glu Ala Gln Tyr Tyr Val Asn Val Asp Trp Val
                325                 330                 335

Gly Gly Ile Tyr Gly Ser Pro Thr Leu Ala Gly Ser Arg Pro Gly Ala
            340                 345                 350

Ile Ile Val Gly Cys Trp Ala Thr Leu Ile Lys Ile Gly Asp Glu Gly
        355                 360                 365

Tyr Lys Lys Ser Cys Lys Asp Ile Val Gly Ala Ala Arg Lys Leu Lys
    370                 375                 380

Leu Arg Ile Gln Lys Glu Ile Pro Glu Leu Glu Ile Ile Gly Asp Pro
385                 390                 395                 400

Leu Thr Ser Val Ile Ser Phe Lys Ser Glu Lys Ile Asn Ile Tyr Glu
                405                 410                 415

Leu Ser Asp Leu Leu Ser Ser Lys Gly Trp His Leu Ser Ala Leu Gln
            420                 425                 430

Lys Pro Ala Ala Leu His Leu Ala Val Thr Arg Leu Ser Val Pro Val
        435                 440                 445

Ile Asp Glu Leu Val Asp Glu Leu Lys Thr Ala Val His Lys Leu Arg
    450                 455                 460

Asp Ser Ser Ala Ala Lys Gly Asp Thr Ala Ala Leu Tyr Gly Val Ala
465                 470                 475                 480

Gly Ser Val Ser Thr Thr Gly Val Val Asp Arg Leu Val Val Gly Phe
                485                 490                 495

Leu Asp Thr Leu Tyr Lys Thr Lys
            500

<210> SEQ ID NO 11
<211> LENGTH: 576
<212> TYPE: DNA
<213> ORGANISM: Pichia ciferrii
<220> FEATURE:
<221> NAME/KEY: CDS
<222> LOCATION: (1)..(576)

<400> SEQUENCE: 11 atg act aca aca cat gaa cca att tct gtt gat gga tca tta tca cca      48
Met Thr Thr Thr His Glu Pro Ile Ser Val Asp Gly Ser Leu Ser Pro
1               5                   10                  15 aat tca aat aca aat aat aat aat caa cat cgt cgt cgt tca tca tca      96
Asn Ser Asn Thr Asn Asn Asn Asn Gln His Arg Arg Arg Ser Ser Ser
            20                  25                  30 ata att tct cat gtt gaa cct gaa act ttt gaa gaa aaa att gat caa     144
Ile Ile Ser His Val Glu Pro Glu Thr Phe Glu Glu Lys Ile Asp Gln
        35                  40                  45 gat tca aca cca aat tta aat gca aat tgg gtt cat tca aaa ggt gct     192
Asp Ser Thr Pro Asn Leu Asn Ala Asn Trp Val His Ser Lys Gly Ala
    50                  55                  60 tgg tta gtt cat att gtt att ata tta tta tta aaa att ttc ttt gat     240
Trp Leu Val His Ile Val Ile Ile Leu Leu Leu Lys Ile Phe Phe Asp
65                  70                  75                  80 tta ata cct ggt tta tca aat gaa att agt tgg tca tta aca aat gct     288
Leu Ile Pro Gly Leu Ser Asn Glu Ile Ser Trp Ser Leu Thr Asn Ala
                85                  90                  95
```

```
aca tat gtt att ggt tca tat att atg ttt cat tta gtt aaa ggt acg    336
Thr Tyr Val Ile Gly Ser Tyr Ile Met Phe His Leu Val Lys Gly Thr
            100                 105                 110 cca ttt gaa ttt aat tca ggt gct tat gat aat tta aca atg tgg gaa    384
Pro Phe Glu Phe Asn Ser Gly Ala Tyr Asp Asn Leu Thr Met Trp Glu
            115                 120                 125 caa tta gat gag gga gat ttt tat aca cca agt aaa aaa ttc tta gtt    432
Gln Leu Asp Glu Gly Asp Phe Tyr Thr Pro Ser Lys Lys Phe Leu Val
130                 135                 140 ggt gta cca att tgg tta ttt ctt tgt tca act cat tat agt cat tat    480
Gly Val Pro Ile Trp Leu Phe Leu Cys Ser Thr His Tyr Ser His Tyr
145                 150                 155                 160 gat tta aaa tta ttt att ata aat tta tta att tgt gct gtt ggt gtt    528
Asp Leu Lys Leu Phe Ile Ile Asn Leu Leu Ile Cys Ala Val Gly Val
                165                 170                 175 gta cca aaa att cca att ttt gat cgt tta aga att aca ttt ttt taa    576
Val Pro Lys Ile Pro Ile Phe Asp Arg Leu Arg Ile Thr Phe Phe
                180                 185                 190

<210> SEQ ID NO 12
<211> LENGTH: 191
<212> TYPE: PRT
<213> ORGANISM: Pichia ciferrii

<400> SEQUENCE: 12

Met Thr Thr Thr His Glu Pro Ile Ser Val Asp Gly Ser Leu Ser Pro
1               5                   10                  15

Asn Ser Asn Thr Asn Asn Asn Gln His Arg Arg Arg Ser Ser Ser
            20                  25                  30

Ile Ile Ser His Val Glu Pro Glu Thr Phe Glu Glu Lys Ile Asp Gln
        35                  40                  45

Asp Ser Thr Pro Asn Leu Asn Ala Asn Trp Val His Ser Lys Gly Ala
    50                  55                  60

Trp Leu Val His Ile Val Ile Leu Leu Lys Ile Phe Phe Asp
65                  70                  75                  80

Leu Ile Pro Gly Leu Ser Asn Glu Ile Ser Trp Ser Leu Thr Asn Ala
                85                  90                  95

Thr Tyr Val Ile Gly Ser Tyr Ile Met Phe His Leu Val Lys Gly Thr
            100                 105                 110

Pro Phe Glu Phe Asn Ser Gly Ala Tyr Asp Asn Leu Thr Met Trp Glu
        115                 120                 125

Gln Leu Asp Glu Gly Asp Phe Tyr Thr Pro Ser Lys Lys Phe Leu Val
130                 135                 140

Gly Val Pro Ile Trp Leu Phe Leu Cys Ser Thr His Tyr Ser His Tyr
145                 150                 155                 160

Asp Leu Lys Leu Phe Ile Ile Asn Leu Leu Ile Cys Ala Val Gly Val
                165                 170                 175

Val Pro Lys Ile Pro Ile Phe Asp Arg Leu Arg Ile Thr Phe Phe
                180                 185                 190

<210> SEQ ID NO 13
<211> LENGTH: 1713
<212> TYPE: DNA
<213> ORGANISM: Pichia ciferrii
<220> FEATURE:
<221> NAME/KEY: CDS
<222> LOCATION: (1)..(1713)

<400> SEQUENCE: 13
```

```
atg aac gtc act gct aca act ata aca act tca aca aca att gca         48
Met Asn Val Thr Ala Thr Thr Ile Thr Thr Ser Thr Thr Ile Ala
1               5                   10                  15 tta caa gat att tgg aat aca act tct gat gtt gtt tct cgt tat tta     96
Leu Gln Asp Ile Trp Asn Thr Thr Ser Asp Val Val Ser Arg Tyr Leu
                20                  25                  30 ttc att ata tta aat tat att gaa tta ata cct ggt gga tca att tta    144
Phe Ile Ile Leu Asn Tyr Ile Glu Leu Ile Pro Gly Gly Ser Ile Leu
            35                  40                  45 gtt cgt tat ata aaa tct tct cat aaa aat gat cca att aga act tta    192
Val Arg Tyr Ile Lys Ser Ser His Lys Asn Asp Pro Ile Arg Thr Leu
        50                  55                  60 ttt gaa att gct tta ttt att ttt gca att aga tat ttt act aca gca    240
Phe Glu Ile Ala Leu Phe Ile Phe Ala Ile Arg Tyr Phe Thr Thr Ala
65                  70                  75                  80 aaa tat gaa aga tct aaa aaa gat cat att aaa ttg aaa aat tct gaa    288
Lys Tyr Glu Arg Ser Lys Lys Asp His Ile Lys Leu Lys Asn Ser Glu
                85                  90                  95 att gat gaa tta att gat gat tgg atg ccg gaa cct tta gtt ttg gat    336
Ile Asp Glu Leu Ile Asp Asp Trp Met Pro Glu Pro Leu Val Leu Asp
            100                 105                 110 att agt cca aag gaa caa tgg caa tta aat tca att cca att gtt aaa    384
Ile Ser Pro Lys Glu Gln Trp Gln Leu Asn Ser Ile Pro Ile Val Lys
        115                 120                 125 ggt cca ata gat act aaa gtg aac cta gtt ggt gaa gaa ggt gac ttt    432
Gly Pro Ile Asp Thr Lys Val Asn Leu Val Gly Glu Glu Gly Asp Phe
    130                 135                 140 tta aat ttt gct tct tca aat ttt tta aat ttt ggt att aat cca att    480
Leu Asn Phe Ala Ser Ser Asn Phe Leu Asn Phe Gly Ile Asn Pro Ile
145                 150                 155                 160 gtt aaa aat gaa tgt aaa aaa att att cat agt aat ggt gtt ggt gct    528
Val Lys Asn Glu Cys Lys Lys Ile Ile His Ser Asn Gly Val Gly Ala
                165                 170                 175 tgt ggt cca cca aat ttt tat ggt aat caa gat att cat att aaa tta    576
Cys Gly Pro Pro Asn Phe Tyr Gly Asn Gln Asp Ile His Ile Lys Leu
            180                 185                 190 gaa aat gat tta gca aaa ttt ttc gaa gtt ggt ggt gct gta tta tat    624
Glu Asn Asp Leu Ala Lys Phe Phe Glu Val Gly Gly Ala Val Leu Tyr
        195                 200                 205 ggt caa gat ttt tgt act gca ggt tca gtt tta cca agt ttt tta aaa    672
Gly Gln Asp Phe Cys Thr Ala Gly Ser Val Leu Pro Ser Phe Leu Lys
    210                 215                 220 aga ggt gat ttt gtt att gct gat gct tca tca aat gtt gca att caa    720
Arg Gly Asp Phe Val Ile Ala Asp Ala Ser Ser Asn Val Ala Ile Gln
225                 230                 235                 240 aaa gct tta caa tta tca aga tgt gaa att tat tgg ttt aat cat aat    768
Lys Ala Leu Gln Leu Ser Arg Cys Glu Ile Tyr Trp Phe Asn His Asn
                245                 250                 255 gat ttg gat cat tta gaa gaa att tta att gat tta caa aaa aat att    816
Asp Leu Asp His Leu Glu Glu Ile Leu Ile Asp Leu Gln Lys Asn Ile
            260                 265                 270 ttt aaa ttt gaa aaa cca att tca aga aaa ttt att gtt act gaa ggt    864
Phe Lys Phe Glu Lys Pro Ile Ser Arg Lys Phe Ile Val Thr Glu Gly
        275                 280                 285 att ttt gca aat aaa ggt gat tca cca tat tta cca aga tta att gaa    912
Ile Phe Ala Asn Lys Gly Asp Ser Pro Tyr Leu Pro Arg Leu Ile Glu
    290                 295                 300 tta aag aaa aaa ttt aaa ttt aga tta ttt ttg gat gaa tct tta tct    960
Leu Lys Lys Lys Phe Lys Phe Arg Leu Phe Leu Asp Glu Ser Leu Ser
```

```
                305                 310                 315                 320
tta ggt gtt tta ggt aaa tct ggt aaa ggt tta gct gaa cat tat aat      1008
Leu Gly Val Leu Gly Lys Ser Gly Lys Gly Leu Ala Glu His Tyr Asn
                325                 330                 335 att aaa aga tca gaa att gat gta act ata agt tca atg gct aat tca      1056
Ile Lys Arg Ser Glu Ile Asp Val Thr Ile Ser Ser Met Ala Asn Ser
            340                 345                 350 ttc tct tct tca ggt gct ttt tgt att ggt gat aaa gtt atg act tat      1104
Phe Ser Ser Ser Gly Ala Phe Cys Ile Gly Asp Lys Val Met Thr Tyr
        355                 360                 365 cat caa aga att ggt tca atg gct tat tgt ttt agt gct tca tta cct      1152
His Gln Arg Ile Gly Ser Met Ala Tyr Cys Phe Ser Ala Ser Leu Pro
    370                 375                 380 gct tat gtt gca aga gct aca tca gtt gca tta aga tta tta act gat      1200
Ala Tyr Val Ala Arg Ala Thr Ser Val Ala Leu Arg Leu Leu Thr Asp
385                 390                 395                 400 tct caa gat tcc cag ggt gaa tca tca att gta aaa aaa tta caa tca      1248
Ser Gln Asp Ser Gln Gly Glu Ser Ser Ile Val Lys Lys Leu Gln Ser
                405                 410                 415 aat aat tat caa tta ttt aat tta ttt aat aaa gat aga aaa tta agt      1296
Asn Asn Tyr Gln Leu Phe Asn Leu Phe Asn Lys Asp Arg Lys Leu Ser
            420                 425                 430 aaa tat tta aaa att ata tca aat gaa att tca cca att tta cat ttt      1344
Lys Tyr Leu Lys Ile Ile Ser Asn Glu Ile Ser Pro Ile Leu His Phe
        435                 440                 445 gaa att aat tca gat tta aga aaa ctt tta aat ttc cca att agt tat      1392
Glu Ile Asn Ser Asp Leu Arg Lys Leu Leu Asn Phe Pro Ile Ser Tyr
    450                 455                 460 aca ggt aaa gga tca gaa att gaa tat aaa aat aaa aaa gga att tct      1440
Thr Gly Lys Gly Ser Glu Ile Glu Tyr Lys Asn Lys Lys Gly Ile Ser
465                 470                 475                 480 gat aaa ttt gtt gaa tca ttt aat tat gaa aat tta att ttt caa aaa      1488
Asp Lys Phe Val Glu Ser Phe Asn Tyr Glu Asn Leu Ile Phe Gln Lys
                485                 490                 495 att ata aat tta tcc aag aaa caa ggt att tta ata aca aga tca att      1536
Ile Ile Asn Leu Ser Lys Lys Gln Gly Ile Leu Ile Thr Arg Ser Ile
            500                 505                 510 ttt aca att gaa caa gaa gct ctg cct ctg att cca aat tta aaa att      1584
Phe Thr Ile Glu Gln Glu Ala Leu Pro Leu Ile Pro Asn Leu Lys Ile
        515                 520                 525 cat tca aat gtt gat ttt act aag gat gaa att gaa aaa gtt tat aaa      1632
His Ser Asn Val Asp Phe Thr Lys Asp Glu Ile Glu Lys Val Tyr Lys
    530                 535                 540 att gtt tcc aaa gta att tta gat gtt ttt gaa aat tta act gtt gaa      1680
Ile Val Ser Lys Val Ile Leu Asp Val Phe Glu Asn Leu Thr Val Glu
545                 550                 555                 560 tca tta tca tta tta act gaa gaa gtt att taa                          1713
Ser Leu Ser Leu Leu Thr Glu Glu Val Ile
                565                 570

<210> SEQ ID NO 14
<211> LENGTH: 570
<212> TYPE: PRT
<213> ORGANISM: Pichia ciferrii

<400> SEQUENCE: 14

Met Asn Val Thr Ala Thr Thr Ile Thr Thr Ser Thr Thr Thr Ile Ala
1               5                   10                  15

Leu Gln Asp Ile Trp Asn Thr Thr Ser Asp Val Val Ser Arg Tyr Leu
            20                  25                  30
```

-continued

```
Phe Ile Ile Leu Asn Tyr Ile Glu Leu Ile Pro Gly Gly Ser Ile Leu
            35                  40                  45

Val Arg Tyr Ile Lys Ser Ser His Lys Asn Asp Pro Ile Arg Thr Leu
 50                  55                  60

Phe Glu Ile Ala Leu Phe Ile Phe Ala Ile Arg Tyr Phe Thr Thr Ala
 65                  70                  75                  80

Lys Tyr Glu Arg Ser Lys Lys Asp His Ile Lys Leu Lys Asn Ser Glu
                 85                  90                  95

Ile Asp Glu Leu Ile Asp Asp Trp Met Pro Glu Pro Leu Val Leu Asp
            100                 105                 110

Ile Ser Pro Lys Glu Gln Trp Gln Leu Asn Ser Ile Pro Ile Val Lys
            115                 120                 125

Gly Pro Ile Asp Thr Lys Val Asn Leu Val Gly Glu Glu Gly Asp Phe
130                 135                 140

Leu Asn Phe Ala Ser Ser Asn Phe Leu Asn Phe Gly Ile Asn Pro Ile
145                 150                 155                 160

Val Lys Asn Glu Cys Lys Lys Ile Ile His Ser Asn Gly Val Gly Ala
                 165                 170                 175

Cys Gly Pro Pro Asn Phe Tyr Gly Asn Gln Asp Ile His Ile Lys Leu
            180                 185                 190

Glu Asn Asp Leu Ala Lys Phe Phe Glu Val Gly Gly Ala Val Leu Tyr
            195                 200                 205

Gly Gln Asp Phe Cys Thr Ala Gly Ser Val Leu Pro Ser Phe Leu Lys
210                 215                 220

Arg Gly Asp Phe Val Ile Ala Asp Ala Ser Asn Val Ala Ile Gln
225                 230                 235                 240

Lys Ala Leu Gln Leu Ser Arg Cys Glu Ile Tyr Trp Phe Asn His Asn
                 245                 250                 255

Asp Leu Asp His Leu Glu Glu Ile Leu Ile Asp Leu Gln Lys Asn Ile
            260                 265                 270

Phe Lys Phe Glu Lys Pro Ile Ser Arg Lys Phe Ile Val Thr Glu Gly
            275                 280                 285

Ile Phe Ala Asn Lys Gly Asp Ser Pro Tyr Leu Pro Arg Leu Ile Glu
290                 295                 300

Leu Lys Lys Lys Phe Lys Phe Arg Leu Phe Leu Asp Glu Ser Leu Ser
305                 310                 315                 320

Leu Gly Val Leu Gly Lys Ser Gly Lys Gly Leu Ala Glu His Tyr Asn
                 325                 330                 335

Ile Lys Arg Ser Glu Ile Asp Val Thr Ile Ser Ser Met Ala Asn Ser
            340                 345                 350

Phe Ser Ser Ser Gly Ala Phe Cys Ile Gly Asp Lys Val Met Thr Tyr
            355                 360                 365

His Gln Arg Ile Gly Ser Met Ala Tyr Cys Phe Ser Ala Ser Leu Pro
370                 375                 380

Ala Tyr Val Ala Arg Ala Thr Ser Val Ala Leu Arg Leu Leu Thr Asp
385                 390                 395                 400

Ser Gln Asp Ser Gln Gly Glu Ser Ser Ile Val Lys Lys Leu Gln Ser
                 405                 410                 415

Asn Asn Tyr Gln Leu Phe Asn Leu Phe Asn Lys Asp Arg Lys Leu Ser
            420                 425                 430

Lys Tyr Leu Lys Ile Ile Ser Asn Glu Ile Ser Pro Ile Leu His Phe
            435                 440                 445
```

```
Glu Ile Asn Ser Asp Leu Arg Lys Leu Leu Asn Phe Pro Ile Ser Tyr
    450                 455                 460
Thr Gly Lys Gly Ser Glu Ile Glu Tyr Lys Asn Lys Lys Gly Ile Ser
465                 470                 475                 480
Asp Lys Phe Val Glu Ser Phe Asn Tyr Glu Asn Leu Ile Phe Gln Lys
                485                 490                 495
Ile Ile Asn Leu Ser Lys Lys Gln Gly Ile Leu Ile Thr Arg Ser Ile
            500                 505                 510
Phe Thr Ile Glu Gln Glu Ala Leu Pro Leu Ile Pro Asn Leu Lys Ile
        515                 520                 525
His Ser Asn Val Asp Phe Thr Lys Asp Glu Ile Glu Lys Val Tyr Lys
    530                 535                 540
Ile Val Ser Lys Val Ile Leu Asp Val Phe Glu Asn Leu Thr Val Glu
545                 550                 555                 560
Ser Leu Ser Leu Leu Thr Glu Glu Val Ile
                565                 570

<210> SEQ ID NO 15
<211> LENGTH: 1689
<212> TYPE: DNA
<213> ORGANISM: Pichia ciferrii
<220> FEATURE:
<221> NAME/KEY: CDS
<222> LOCATION: (1)..(1689)

<400> SEQUENCE: 15
```

| | | | | | | | | | | | | | | | | |
|---|---|---|---|---|---|---|---|---|---|---|---|---|---|---|---|---|
| atg | tca | ttg | gta | ata | cct | caa | ata | gat | cta | tca | ggt | ctt | tcc | atc | gaa | 48 |
| Met | Ser | Leu | Val | Ile | Pro | Gln | Ile | Asp | Leu | Ser | Gly | Leu | Ser | Ile | Glu | |
| 1 | | | | 5 | | | | | 10 | | | | | 15 | | |
| gac | aag | aaa | caa | aat | gaa | ttc | ggt | gct | cta | act | tca | aat | gaa | tat | cgt | 96 |
| Asp | Lys | Lys | Gln | Asn | Glu | Phe | Gly | Ala | Leu | Thr | Ser | Asn | Glu | Tyr | Arg | |
| | | | 20 | | | | | 25 | | | | | 30 | | | |
| tac | aaa | aca | att | tca | aga | cag | ggg | aaa | cca | tta | cct | gat | cca | att | gaa | 144 |
| Tyr | Lys | Thr | Ile | Ser | Arg | Gln | Gly | Lys | Pro | Leu | Pro | Asp | Pro | Ile | Glu | |
| | | 35 | | | | | 40 | | | | | 45 | | | | |
| gat | gaa | cca | cca | tat | cat | gtc | ctt | ttc | atc | act | tat | tta | aac | tat | tta | 192 |
| Asp | Glu | Pro | Pro | Tyr | His | Val | Leu | Phe | Ile | Thr | Tyr | Leu | Asn | Tyr | Leu | |
| | 50 | | | | | 55 | | | | | 60 | | | | | |
| atc | ttg | att | atc | gtt | ggt | cat | att | aaa | gat | ttc | aca | ggt | att | ctg | ttc | 240 |
| Ile | Leu | Ile | Ile | Val | Gly | His | Ile | Lys | Asp | Phe | Thr | Gly | Ile | Leu | Phe | |
| 65 | | | | | 70 | | | | | 75 | | | | | 80 | |
| aac | cca | aaa | aat | tac | caa | gat | tta | tta | gaa | caa | aat | ggc | ctt | gct | cca | 288 |
| Asn | Pro | Lys | Asn | Tyr | Gln | Asp | Leu | Leu | Glu | Gln | Asn | Gly | Leu | Ala | Pro | |
| | | | 85 | | | | | 90 | | | | | 95 | | | |
| tgg | tat | aat | aaa | ttt | gaa | agt | ttt | tat | att | cgt | cgt | atg | aaa | caa | aaa | 336 |
| Trp | Tyr | Asn | Lys | Phe | Glu | Ser | Phe | Tyr | Ile | Arg | Arg | Met | Lys | Gln | Lys | |
| | | | 100 | | | | | 105 | | | | | 110 | | | |
| att | gat | gat | tgt | ttt | gca | aga | cca | act | tgt | ggt | gtc | cca | ggt | aga | tta | 384 |
| Ile | Asp | Asp | Cys | Phe | Ala | Arg | Pro | Thr | Cys | Gly | Val | Pro | Gly | Arg | Leu | |
| | | 115 | | | | | 120 | | | | | 125 | | | | |
| atc | act | tgt | att | gat | cgt | gat | gct | cat | gat | tat | aat | tca | tat | ttt | agt | 432 |
| Ile | Thr | Cys | Ile | Asp | Arg | Asp | Ala | His | Asp | Tyr | Asn | Ser | Tyr | Phe | Ser | |
| | 130 | | | | | 135 | | | | | 140 | | | | | |
| tat | cct | ggt | act | act | tca | act | tgt | tta | aat | tta | tca | tca | tat | aat | tat | 480 |
| Tyr | Pro | Gly | Thr | Thr | Ser | Thr | Cys | Leu | Asn | Leu | Ser | Ser | Tyr | Asn | Tyr | |
| 145 | | | | | 150 | | | | | 155 | | | | | 160 | |
| ttg | ggg | ttt | gca | caa | tct | gaa | ggg | gca | tgt | act | caa | gcc | gct | tta | gaa | 528 |
| Leu | Gly | Phe | Ala | Gln | Ser | Glu | Gly | Ala | Cys | Thr | Gln | Ala | Ala | Leu | Glu | |
| | | | 165 | | | | | 170 | | | | | 175 | | | |

```
att ttg gat tat tat ggt gtt ggt tct ggt ggt cca aga aat gtt att    576
Ile Leu Asp Tyr Tyr Gly Val Gly Ser Gly Gly Pro Arg Asn Val Ile
            180                 185                 190 ggt act act gat tta cat tta aaa act gaa aaa act ata gca aaa ttt    624
Gly Thr Thr Asp Leu His Leu Lys Thr Glu Lys Thr Ile Ala Lys Phe
        195                 200                 205 att ggt aaa gat gat tca atc tta ttt tca atg ggg tat gca aca aat    672
Ile Gly Lys Asp Asp Ser Ile Leu Phe Ser Met Gly Tyr Ala Thr Asn
    210                 215                 220 gca agt tta ttt agt tct tta ttg gat aag aaa tca ctt gtt att tct    720
Ala Ser Leu Phe Ser Ser Leu Leu Asp Lys Lys Ser Leu Val Ile Ser
225                 230                 235                 240 gat gaa tta aat cat gct tca att aga act ggt gtt aga tta tct ggt    768
Asp Glu Leu Asn His Ala Ser Ile Arg Thr Gly Val Arg Leu Ser Gly
            245                 250                 255 tct aca gtt aaa act ttc cct cat aat aat atg att gcc ttg gaa aaa    816
Ser Thr Val Lys Thr Phe Pro His Asn Asn Met Ile Ala Leu Glu Lys
        260                 265                 270 att ctt aga gaa caa att tct caa ggt caa cca aga tct cat cgt cca    864
Ile Leu Arg Glu Gln Ile Ser Gln Gly Gln Pro Arg Ser His Arg Pro
    275                 280                 285 tgg aaa aaa atc att gtt gca gtt gaa ggg ctt tat tca atg gag ggt    912
Trp Lys Lys Ile Ile Val Ala Val Glu Gly Leu Tyr Ser Met Glu Gly
290                 295                 300 aca atg gca aat tta cct gca tta att gaa tta aga aga aaa tat aaa    960
Thr Met Ala Asn Leu Pro Ala Leu Ile Glu Leu Arg Arg Lys Tyr Lys
305                 310                 315                 320 ttt aat tta ttt gtt gat gaa gct cat tca att ggt gct att ggt cca    1008
Phe Asn Leu Phe Val Asp Glu Ala His Ser Ile Gly Ala Ile Gly Pro
            325                 330                 335 tca ggt cgt ggt gtt tgt gat tat ttt ggt ata gat ccc tca aat gtt    1056
Ser Gly Arg Gly Val Cys Asp Tyr Phe Gly Ile Asp Pro Ser Asn Val
        340                 345                 350 gat tta tta atg ggg act tta act aaa tca ttt ggt gct gca ggt ggt    1104
Asp Leu Leu Met Gly Thr Leu Thr Lys Ser Phe Gly Ala Ala Gly Gly
    355                 360                 365 tat att gct ggt tca caa caa att ata aat cgt tta aaa tta aat att    1152
Tyr Ile Ala Gly Ser Gln Gln Ile Ile Asn Arg Leu Lys Leu Asn Ile
370                 375                 380 aat tca caa aat tat gca gaa tct atc cct gca cct gtt ttg gca caa    1200
Asn Ser Gln Asn Tyr Ala Glu Ser Ile Pro Ala Pro Val Leu Ala Gln
385                 390                 395                 400 att att tct tcg tta aat atc atc tcg ggt gat tta aat cct ggt gaa    1248
Ile Ile Ser Ser Leu Asn Ile Ile Ser Gly Asp Leu Asn Pro Gly Glu
            405                 410                 415 ggt tcg gaa aga tta gaa aga att gct ttt aat tca cgt tat tta aga    1296
Gly Ser Glu Arg Leu Glu Arg Ile Ala Phe Asn Ser Arg Tyr Leu Arg
        420                 425                 430 tta ggt tta caa aga tta ggt ttt atc gta tac gga gtt gat gat tca    1344
Leu Gly Leu Gln Arg Leu Gly Phe Ile Val Tyr Gly Val Asp Asp Ser
    435                 440                 445 cca gtg att cca tta tta tta ttc gcc cca gcc aaa atg cca gca ttt    1392
Pro Val Ile Pro Leu Leu Leu Phe Ala Pro Ala Lys Met Pro Ala Phe
450                 455                 460 tca cgt atg cta tat caa aga aaa att gca gtt gtt gtt gtt gga tac    1440
Ser Arg Met Leu Tyr Gln Arg Lys Ile Ala Val Val Val Val Gly Tyr
465                 470                 475                 480 ccg gca act cca ctg act tca tca aga gtt cgt ctt tgt gtt tct gca    1488
Pro Ala Thr Pro Leu Thr Ser Ser Arg Val Arg Leu Cys Val Ser Ala
            485                 490                 495
```

```
tct tta aca aaa gaa gat att gat tat ctt tta cgt cat tta tcc gag    1536
Ser Leu Thr Lys Glu Asp Ile Asp Tyr Leu Leu Arg His Leu Ser Glu
            500                 505                 510 gtg ggt gat aaa tta ttt tta aaa ttt agt tct ggt att gct ggt ggt    1584
Val Gly Asp Lys Leu Phe Leu Lys Phe Ser Ser Gly Ile Ala Gly Gly
        515                 520                 525 tct tta gat ggt tca cca cca aga tgg aat att gaa gat gtt ttg aaa    1632
Ser Leu Asp Gly Ser Pro Pro Arg Trp Asn Ile Glu Asp Val Leu Lys
530                 535                 540 gag act cca aag gat tgt aaa gaa tct aaa tat ttt att gca act gca    1680
Glu Thr Pro Lys Asp Cys Lys Glu Ser Lys Tyr Phe Ile Ala Thr Ala
545                 550                 555                 560 aat aat tga                                                        1689
Asn Asn
```

<210> SEQ ID NO 16
<211> LENGTH: 562
<212> TYPE: PRT
<213> ORGANISM: Pichia ciferrii

<400> SEQUENCE: 16

```
Met Ser Leu Val Ile Pro Gln Ile Asp Leu Ser Gly Leu Ser Ile Glu
1               5                   10                  15

Asp Lys Lys Gln Asn Glu Phe Gly Ala Leu Thr Ser Asn Glu Tyr Arg
            20                  25                  30

Tyr Lys Thr Ile Ser Arg Gln Gly Lys Pro Leu Pro Asp Pro Ile Glu
        35                  40                  45

Asp Glu Pro Pro Tyr His Val Leu Phe Ile Thr Tyr Leu Asn Tyr Leu
    50                  55                  60

Ile Leu Ile Ile Val Gly His Ile Lys Asp Phe Thr Gly Ile Leu Phe
65                  70                  75                  80

Asn Pro Lys Asn Tyr Gln Asp Leu Leu Glu Gln Asn Gly Leu Ala Pro
                85                  90                  95

Trp Tyr Asn Lys Phe Glu Ser Phe Tyr Ile Arg Arg Met Lys Gln Lys
            100                 105                 110

Ile Asp Asp Cys Phe Ala Arg Pro Thr Cys Gly Val Pro Gly Arg Leu
        115                 120                 125

Ile Thr Cys Ile Asp Arg Asp Ala His Asp Tyr Asn Ser Tyr Phe Ser
    130                 135                 140

Tyr Pro Gly Thr Thr Ser Thr Cys Leu Asn Leu Ser Ser Tyr Asn Tyr
145                 150                 155                 160

Leu Gly Phe Ala Gln Ser Glu Gly Ala Cys Thr Gln Ala Ala Leu Glu
                165                 170                 175

Ile Leu Asp Tyr Tyr Gly Val Gly Ser Gly Gly Pro Arg Asn Val Ile
            180                 185                 190

Gly Thr Thr Asp Leu His Leu Lys Thr Glu Lys Thr Ile Ala Lys Phe
        195                 200                 205

Ile Gly Lys Asp Asp Ser Ile Leu Phe Ser Met Gly Tyr Ala Thr Asn
    210                 215                 220

Ala Ser Leu Phe Ser Ser Leu Leu Asp Lys Lys Ser Leu Val Ile Ser
225                 230                 235                 240

Asp Glu Leu Asn His Ala Ser Ile Arg Thr Gly Val Arg Leu Ser Gly
                245                 250                 255

Ser Thr Val Lys Thr Phe Pro His Asn Asn Met Ile Ala Leu Glu Lys
            260                 265                 270
```

```
Ile Leu Arg Glu Gln Ile Ser Gln Gly Gln Pro Arg Ser His Arg Pro
        275                 280                 285

Trp Lys Lys Ile Ile Val Ala Val Glu Gly Leu Tyr Ser Met Glu Gly
    290                 295                 300

Thr Met Ala Asn Leu Pro Ala Leu Ile Glu Leu Arg Arg Lys Tyr Lys
305                 310                 315                 320

Phe Asn Leu Phe Val Asp Glu Ala His Ser Ile Gly Ala Ile Gly Pro
                325                 330                 335

Ser Gly Arg Gly Val Cys Asp Tyr Phe Gly Ile Asp Pro Ser Asn Val
            340                 345                 350

Asp Leu Leu Met Gly Thr Leu Thr Lys Ser Phe Gly Ala Ala Gly Gly
                355                 360                 365

Tyr Ile Ala Gly Ser Gln Gln Ile Ile Asn Arg Leu Lys Leu Asn Ile
    370                 375                 380

Asn Ser Gln Asn Tyr Ala Glu Ser Ile Pro Ala Pro Val Leu Ala Gln
385                 390                 395                 400

Ile Ile Ser Ser Leu Asn Ile Ile Ser Gly Asp Leu Asn Pro Gly Glu
                405                 410                 415

Gly Ser Glu Arg Leu Glu Arg Ile Ala Phe Asn Ser Arg Tyr Leu Arg
            420                 425                 430

Leu Gly Leu Gln Arg Leu Gly Phe Ile Val Tyr Gly Val Asp Asp Ser
    435                 440                 445

Pro Val Ile Pro Leu Leu Phe Ala Pro Ala Lys Met Pro Ala Phe
                450                 455                 460

Ser Arg Met Leu Tyr Gln Arg Lys Ile Ala Val Val Val Gly Tyr
465                 470                 475                 480

Pro Ala Thr Pro Leu Thr Ser Ser Arg Val Arg Leu Cys Val Ser Ala
                485                 490                 495

Ser Leu Thr Lys Glu Asp Ile Asp Tyr Leu Leu Arg His Leu Ser Glu
            500                 505                 510

Val Gly Asp Lys Leu Phe Leu Lys Phe Ser Ser Gly Ile Ala Gly Gly
    515                 520                 525

Ser Leu Asp Gly Ser Pro Pro Arg Trp Asn Ile Glu Asp Val Leu Lys
530                 535                 540

Glu Thr Pro Lys Asp Cys Lys Glu Ser Lys Tyr Phe Ile Ala Thr Ala
545                 550                 555                 560

Asn Asn

<210> SEQ ID NO 17
<211> LENGTH: 978
<212> TYPE: DNA
<213> ORGANISM: Pichia ciferrii
<220> FEATURE:
<221> NAME/KEY: CDS
<222> LOCATION: (1)..(978)

<400> SEQUENCE: 17 atg agc tct cat cag ttt ttg atc aac caa aca act ttg gcg gct cca    48
Met Ser Ser His Gln Phe Leu Ile Asn Gln Thr Thr Leu Ala Ala Pro
1               5                   10                  15 cct gtt cat ttg gtg gag aaa cca agt ttg att aat ggc ata ccg gat    96
Pro Val His Leu Val Glu Lys Pro Ser Leu Ile Asn Gly Ile Pro Asp
                20                  25                  30 aac att tta gcc ttg att gca cct gtt ata gct tat tat tca tat tca   144
Asn Ile Leu Ala Leu Ile Ala Pro Val Ile Ala Tyr Tyr Ser Tyr Ser
            35                  40                  45
```

```
gga ttt ttc tat gtg att gat act tta gaa att gca gaa ctt tat aga      192
Gly Phe Phe Tyr Val Ile Asp Thr Leu Glu Ile Ala Glu Leu Tyr Arg
 50                  55                  60 att cat cca cct gaa gaa gtt agt tca aga aat aaa gct aca aaa ttt      240
Ile His Pro Pro Glu Glu Val Ser Ser Arg Asn Lys Ala Thr Lys Phe
 65                  70                  75                  80 gat gtt tta aaa gat gtt gtt tta caa cat ttt ata cag agt gtt gtt      288
Asp Val Leu Lys Asp Val Val Leu Gln His Phe Ile Gln Ser Val Val
                 85                  90                  95 ggt tat atc ttt aca tat ttt gat cca att caa tat act ggt gat gaa      336
Gly Tyr Ile Phe Thr Tyr Phe Asp Pro Ile Gln Tyr Thr Gly Asp Glu
            100                 105                 110 gaa tat caa gct tgg aaa tta caa caa act tta cca ttt tta cca ttt      384
Glu Tyr Gln Ala Trp Lys Leu Gln Gln Thr Leu Pro Phe Leu Pro Phe
        115                 120                 125 gat gtt gca tat tat tgg aat atg tat ggt tgg agt tgt ttg aaa att      432
Asp Val Ala Tyr Tyr Trp Asn Met Tyr Gly Trp Ser Cys Leu Lys Ile
130                 135                 140 ggt ctt gca ttt tta att att gat tca tgg caa tat tgg tta cat aga      480
Gly Leu Ala Phe Leu Ile Ile Asp Ser Trp Gln Tyr Trp Leu His Arg
145                 150                 155                 160 att atg cat tta aac aag aca tta tac aaa aga ttc cat tca aga cat      528
Ile Met His Leu Asn Lys Thr Leu Tyr Lys Arg Phe His Ser Arg His
                165                 170                 175 cat cgt ctt tat gtc cca tat gct ttt ggt gct tta tat aat gat cca      576
His Arg Leu Tyr Val Pro Tyr Ala Phe Gly Ala Leu Tyr Asn Asp Pro
            180                 185                 190 ttt gaa ggg ttt tta ttg gat acc tta ggt acc ggt att gct gca att      624
Phe Glu Gly Phe Leu Leu Asp Thr Leu Gly Thr Gly Ile Ala Ala Ile
        195                 200                 205 gtt act caa tta act cca aga gaa tct att gtt tta tat aca ttt tca      672
Val Thr Gln Leu Thr Pro Arg Glu Ser Ile Val Leu Tyr Thr Phe Ser
210                 215                 220 act ttg aaa act gtt gat gat cat tgt ggt tat tca tta cct tat gat      720
Thr Leu Lys Thr Val Asp Asp His Cys Gly Tyr Ser Leu Pro Tyr Asp
225                 230                 235                 240 cct ttc caa att ttg ttc cca aat aac tca att tat cat gat att cat      768
Pro Phe Gln Ile Leu Phe Pro Asn Asn Ser Ile Tyr His Asp Ile His
                245                 250                 255 cat caa caa ttt ggt atc aag acc aat ttt tca caa cct ttc ttt aca      816
His Gln Gln Phe Gly Ile Lys Thr Asn Phe Ser Gln Pro Phe Phe Thr
            260                 265                 270 cat tgg gat gtt ttc agt aat aca aga tat aaa gaa att gat gaa tac      864
His Trp Asp Val Phe Ser Asn Thr Arg Tyr Lys Glu Ile Asp Glu Tyr
        275                 280                 285 aga gaa aag caa aaa gct att aca att gcc aaa tat aaa gag ttt tta      912
Arg Glu Lys Gln Lys Ala Ile Thr Ile Ala Lys Tyr Lys Glu Phe Leu
290                 295                 300 cat gat cgt gaa att gca aaa caa aag aag aag gct gaa att tat aaa      960
His Asp Arg Glu Ile Ala Lys Gln Lys Lys Lys Ala Glu Ile Tyr Lys
305                 310                 315                 320 gat aag aaa act gat tga                                              978
Asp Lys Lys Thr Asp
                325

<210> SEQ ID NO 18
<211> LENGTH: 325
<212> TYPE: PRT
<213> ORGANISM: Pichia ciferrii

<400> SEQUENCE: 18
```

```
Met Ser Ser His Gln Phe Leu Ile Asn Gln Thr Thr Leu Ala Ala Pro
1               5                   10                  15

Pro Val His Leu Val Glu Lys Pro Ser Leu Ile Asn Gly Ile Pro Asp
            20                  25                  30

Asn Ile Leu Ala Leu Ile Ala Pro Val Ile Ala Tyr Tyr Ser Tyr Ser
        35                  40                  45

Gly Phe Phe Tyr Val Ile Asp Thr Leu Glu Ile Ala Glu Leu Tyr Arg
    50                  55                  60

Ile His Pro Pro Glu Glu Val Ser Ser Arg Asn Lys Ala Thr Lys Phe
65                  70                  75                  80

Asp Val Leu Lys Asp Val Val Leu Gln His Phe Ile Gln Ser Val Val
                85                  90                  95

Gly Tyr Ile Phe Thr Tyr Phe Asp Pro Ile Gln Tyr Thr Gly Asp Glu
            100                 105                 110

Glu Tyr Gln Ala Trp Lys Leu Gln Gln Thr Leu Pro Phe Leu Pro Phe
        115                 120                 125

Asp Val Ala Tyr Tyr Trp Asn Met Tyr Gly Trp Ser Cys Leu Lys Ile
    130                 135                 140

Gly Leu Ala Phe Leu Ile Ile Asp Ser Trp Gln Tyr Trp Leu His Arg
145                 150                 155                 160

Ile Met His Leu Asn Lys Thr Leu Tyr Lys Arg Phe His Ser Arg His
                165                 170                 175

His Arg Leu Tyr Val Pro Tyr Ala Phe Gly Ala Leu Tyr Asn Asp Pro
            180                 185                 190

Phe Glu Gly Phe Leu Leu Asp Thr Leu Gly Thr Gly Ile Ala Ala Ile
        195                 200                 205

Val Thr Gln Leu Thr Pro Arg Glu Ser Ile Val Leu Tyr Thr Phe Ser
    210                 215                 220

Thr Leu Lys Thr Val Asp Asp His Cys Gly Tyr Ser Leu Pro Tyr Asp
225                 230                 235                 240

Pro Phe Gln Ile Leu Phe Pro Asn Asn Ser Ile Tyr His Asp Ile His
                245                 250                 255

His Gln Gln Phe Gly Ile Lys Thr Asn Phe Ser Gln Pro Phe Phe Thr
            260                 265                 270

His Trp Asp Val Phe Ser Asn Thr Arg Tyr Lys Glu Ile Asp Glu Tyr
        275                 280                 285

Arg Glu Lys Gln Lys Ala Ile Thr Ile Ala Lys Tyr Lys Glu Phe Leu
    290                 295                 300

His Asp Arg Glu Ile Ala Lys Gln Lys Lys Ala Glu Ile Tyr Lys
305                 310                 315                 320

Asp Lys Lys Thr Asp
                325

<210> SEQ ID NO 19
<211> LENGTH: 1681
<212> TYPE: DNA
<213> ORGANISM: Artificial
<220> FEATURE:
<223> OTHER INFORMATION: Kassette

<400> SEQUENCE: 19
gaaattaata cgactcacta tagggagacc ggcagatccg cggccgcata ggccactagt    60
ggatctgata tcatcgatga attcgagctc ataacttcgt atagcataca ttatacgaag   120
ttattcgaca ctggatggcg gcgttagtat cgaatcgaca gcagtatagc gaccagcatt   180
```

| | |
|---|---|
| cacatacgat tgacgcatga tattactttc tgcgcactta acttcgcatc tgggcagatg | 240 |
| atgtcgaggc gaaaaaaat ataaatcacg ctaacatttg attaaaatag aacaactaca | 300 |
| atataaaaaa actatacaaa tgacaagttc ttgaaaacaa gaatcttttt attgtcagta | 360 |
| ctgattatta tggacatggc attgacatat ataaagcttg ttcaccatct gaagcagtac | 420 |
| catcatataa agcagtatct aaaccacata atgtgaaacc cattcttcta taagcatgaa | 480 |
| tagctggagc attaacatta gtaacttcta accataaatg accagcacca cgttctctag | 540 |
| caaattcagt agctaaaccc attaaagctc taccaacacc atgacctcta tgttctggag | 600 |
| caacttcaat atcttcaaca gttaatcttc tattccaacc tgaatatgaa acaacaacaa | 660 |
| aaccagctaa gtctccgtca tcaccataag caacaaaagt tcttgaatct ggatcaccat | 720 |
| cttcaccgtc atcagactcg tcatctgatt catcatctgg aaaaacttta gttaatggtg | 780 |
| gatcaactgg aacttctctt aaagtaaaac catcaccagt agcagtaact ctaaaaacag | 840 |
| tatcagtagt aaatgaacca tctaaagctt caatagcttc agcatcacct ggaactgaag | 900 |
| ttctatatct ataagcagta tcatctaaag tagtacccat tgataataaa gttgattttg | 960 |
| aagtttggaa agtagtttct ggaacttcta attcataacc ttcaaatgat gaagctggta | 1020 |
| agttaatagt gacaatctgt gtgaaaacgg gttagtaatt aaacattgtc tagtgtttcc | 1080 |
| cactgatttg gattgaaaat ttggtgattt gtggttgtat agatctaaat cttgattgtc | 1140 |
| ccctatcttt cctagatatc aaaaaaacaa tcacaaaaca atcaaagaac caattaaaat | 1200 |
| ccaatcaatt catctccatt atccacaatt catcatcgat ccaaaaatat aataacaatc | 1260 |
| tacttacttc atcatcttgg ttggcttcag tggccatagt tctggcaact ctttgagttg | 1320 |
| atctcaaaga agttgtgttt gaagaggac gaacaatatt cttcaacatc atctttgtat | 1380 |
| agtagtctga actcctccgg gaaagtttag ttgtgttgaa tatttagttg aaaatggggg | 1440 |
| agaattgcaa acctctaata aaagttgaat acttctacta ttttcaaacc aaacaaatta | 1500 |
| tcaattgaat gtattattga attttgaatt caaaatcgat aaatttactt ttcgtttttt | 1560 |
| cgcatcaggt gtttgaaaat ggccggtgcg tcgcgaaccg ggcaaattta gagcacaata | 1620 |
| acttcgtata gcatacatta tacgaagtta tctgcaggtt acccagtggt acgaagcgcc | 1680 |
| a | 1681 |

<210> SEQ ID NO 20
<211> LENGTH: 3872
<212> TYPE: DNA
<213> ORGANISM: Artificial
<220> FEATURE:
<223> OTHER INFORMATION: Kassette

<400> SEQUENCE: 20

| | |
|---|---|
| tgagcaaaag gccagcaaaa ggccaggaac cgtaaaaagg ccgcgttgct ggcgtttttc | 60 |
| cataggctcc gccccctga cgagcatcac aaaaatcgac gctcaagtca gaggtggcga | 120 |
| aacccgacag gactataaag ataccaggcg tttccccctg gaagctccct cgtgcgctct | 180 |
| cctgttccga ccctgccgct taccggatac ctgtccgcct ttctcccttc gggaagcgtg | 240 |
| gcgctttctc aatgctcacg ctgtaggtat ctcagttcgg tgtaggtcgt tcgctccaag | 300 |
| ctgggctgtg tgcacgaacc ccccgttcag cccgaccgct gcgccttatc cggtaactat | 360 |
| cgtcttgagt ccaacccggt aagacacgac ttatcgccac tggcagcagc cactggtaac | 420 |
| aggattagca gagcgaggta tgtaggcggt gctacagagt tcttgaagtg gtggcctaac | 480 |

```
tacggctaca ctagaaggac agtatttggt atctgcgctc tgctgaagcc agttaccttc    540
ggaaaaagag ttggtagctc ttgatccggc aaacaaacca ccgctggtag cggtggtttt    600
tttgtttgca agcagcagat tacgcgcaga aaaaaggat ctcaagaaga tcctttgatc    660
ttttctacgg ggtctgacgc tcagtggaac gaaaactcac gttaagggat tttggtcatg    720
agattatcaa aaaggatctt cacctagatc cttttaaatt aaaaatgaag ttttaaatca    780
atctaaagta tatatgagta aacttggtct gacagttacc aatgcttaat cagtgaggca    840
cctatctcag cgatctgtct atttcgttca tccatagttg cctgactccc cgtcgtgtag    900
ataactacga tacgggaggg cttaccatct ggccccagtg ctgcaatgat accgcgagac    960
ccacgctcac cggctccaga tttatcagca ataaaccagc cagccggaag ggccgagcgc   1020
agaagtggtc ctgcaacttt atccgcctcc atccagtcta ttaattgttg ccgggaagct   1080
agagtaagta gttcgccagt taatagtttg cgcaacgttg ttgccattgc tacaggcatc   1140
gtggtgtcac gctcgtcgtt tggtatggct tcattcagct ccggttccca acgatcaagg   1200
cgagttacat gatcccccat gttgtgcaaa aaagcggtta gctccttcgg tcctccgatc   1260
gttgtcagaa gtaagttggc cgcagtgtta tcactcatgg ttatggcagc actgcataat   1320
tctcttactg tcatgccatc cgtaagatgc ttttctgtga ctggtgagta ctcaaccaag   1380
tcattctgag aatagtgtat gcggcgaccg agttgctctt gcccggcgtc aatacgggat   1440
aataccgcgc cacatagcag aactttaaaa gtgctcatca ttggaaaacg ttcttcgggg   1500
cgaaaactct caaggatctt accgctgttg agatccagtt cgatgtaacc cactcgtgca   1560
cccaactgat cttcagcatc ttttactttc accagcgttt ctgggtgagc aaaaacagga   1620
aggcaaaatg ccgcaaaaaa gggaataagg gcgacacgga aatgttgaat actcatactc   1680
ttcctttttc aatattattg aagcatttat cagggttatt gtctcatgag cggatacata   1740
tttgaatgta tttagaaaaa taaacaaata ggggttccgc gcacatttcc ccgaaaagtg   1800
ccacctgacg tctaagaaac cattattatc atgacattaa cctataaaaa taggcgtatc   1860
acgaggccct ttcgtctcgc gcgtttcggt gatgacggtg aaaacctctg acacatgctg   1920
tgctctaaat tgcccggtt cgcgacgcac cggccatttt caaacacctg atgcgaaaaa   1980
acgaaaagta aatttatcga ttttgaattc aaaattcaat aatacattca attgataatt   2040
tgtttggttt gaaaatagta gaagtattca acttttatta gaggtttgca attctccccc   2100
attttcaact aaatattcaa cacaactaaa cttttcccgga ggagttcaga ctactataca   2160
aagatgatgt tgaagaatat tgttcgtcct cttttcaaaca caacttcttt gagatcaact   2220
caaagagttg ccagaactat ggccactgaa gccaaccaag atgatgaagt aagtagattg   2280
ttattatatt tttggatcga tgatgaattg tggataatgg agatgaattg attggatttt   2340
aattggttct ttgattgttt tgtgattgtt ttttgatat ctaggaaaga tagggacaa    2400 tcaagattta gatctataca accacaaatc accaaatttt caatccaaat cagtgggaaa   2460
cactagacaa tgtttaatta ctaacccgtt ttcacacaga ttgtcactat taacttacca   2520
gcttcatcat ttgaaggtta tgaattagaa gttccagaaa ctactttcca aacttcaaaa   2580
tcaactttat tatcaatgtc aaatttatta actgttcatc aaaatttacc agctttacca   2640
gttgatgcta cttcagatga agttagaaaa aatttaatgg atatgtttag agatagacaa   2700 gcttttttcag aacatacttg gaaaatgtta ttatcagttt gtagatcatg ggctgcttgg   2760
tgtaaattaa taatagaaa atgggtttcca gctgaaccag aagatgttag agattactta   2820
ttatatttac aagctagagg tttagctgtt aaaactattc aacaacactt aggacaatta   2880
```

```
aatatgttac atcgtagatc aggtttacca agaccatcag attcaaatgc tgtttcatta    2940
gttatgagaa gaattagaaa agaaaatgtt gatgctggtg aaagagctaa acaagcttta    3000
gcttttgaaa gaactgattt tgatcaagtt agatcattaa tggaaaattc agatagatgt    3060
caagatatta gaaacttagc ttttttaggt attgcttata atactttatt aagaattgct    3120
gaaattgcta gaattagagt taaagatatt tcaagaactg atggtggtag aatgttaatt    3180
catattggta gaactaaaac tttagtttca actgctggtt tgaaaaagc tttatcatta     3240 ggtgttacta aattagttga aagatggatt tcagtttcag gtgttgctga tgatccaaat    3300
aattacttat tctgtagagt tagaaaaaat ggtgttgctg ctccatcagc tacttcacaa    3360
ttatcaacta gagctttaga aggtattttt gaagctactc atcgtttaat ctatggtgct    3420
aaagatgatt caggtcaaag atacttagct tggagtggac attcagctag agttggtgct    3480
gctagagata tggctagagc tggtgtttca attccagaaa ttatgcaagc tggaggatgg    3540
actaatgtta atattgttat gaattatatt agaaacttag attcagaaac tggtgctatg    3600
gttcgtttat tagaagatgg tgattaatca gtactgacaa taaaaagatt cttgttttca    3660
agaacttgtc atttgtatag ttttttttata ttgtagttgt tctatttttaa tcaaatgtta   3720 gcgtgattta tattttttttt cgcctcgaca tcatctgccc agatgcgaag ttaagtgcgc    3780
agaaagtaat atcatgcgtc aatcgtatgt gaatgctggt cgctatactg ctgtcgattc    3840
gatactaacg ccgccatcca gtgtcgagca tg                                   3872

<210> SEQ ID NO 21
<211> LENGTH: 584
<212> TYPE: DNA
<213> ORGANISM: Pichia ciferrii

<400> SEQUENCE: 21
cagatcaaac cacatcatga gcttcaattg ataaacatga gaacatgaga ttccaattct      60
ttaacgttgt gcgtggcttg acggatccta tatacgctaa cacgctaaac gctaaacgtc     120
aagacgagaa ccaacccgca tcttgccatt gcaggccaa ttcaagagat gttttctgga     180
taattagtgt aaagtgttca attgtgctcg aggaatccaa ccattataac ctcatccttt     240
tgagaacaat agatttggta cttattgtta taaattctat cgcaacttgt cctgtctaac     300
ggtgggaaat tggcatcacc tggtgatgtt ttggccaaca cctgagccat tacccgctgc    360
ttctcagcac catattttgt taaaccactt gatctcacca tacaacgaca ccaccgggta     420
ccacacttgc gttgggcaga aattctcaat tcgccaattc caattgtagt ataaatacat    480
catttattcc ctttttatcag aaactataag taataataga agaattcttt tttcctttct    540
ctatcaattg tactcaattc gataaaacat atacacatta caca                      584

<210> SEQ ID NO 22
<211> LENGTH: 420
<212> TYPE: DNA
<213> ORGANISM: Pichia ciferrii

<400> SEQUENCE: 22
cggaccgtta attaccaaca atctcaattg tacaacatag tgttaaaaca ggataacttg      60
atgattatat gtgatattaa gttcaaacaa gtaccaataa atagataatt aatagctcta    120
taatatatca tttaattgaa ttaatatcaa tagttgttgt ttaattatcc ctagttttct    180
ggttaaagtt acaccatcag atggttcacc accaatgttg ttcaaaccat ttccactcaa    240
```

```
ctgacgtttc aagaacatca cctgaaaaaa aaaaattcat cacacattgg gagaaattgg      300
gagaattgta tataaggagt tgaaatcgct aatatttta tacttctact cacttgtttt      360
aattctacat cagtatttta taatacaaaa acaaacaaac aaacaaataa ttaattaaca     420
```

<210> SEQ ID NO 23
<211> LENGTH: 19
<212> TYPE: DNA
<213> ORGANISM: Artificial Sequence
<220> FEATURE:
<223> OTHER INFORMATION: Primer

<400> SEQUENCE: 23
gcttccggct cctatgttg                                                   19

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
accctatgcg gtgtgaaata c                                                21

<210> SEQ ID NO 25
<211> LENGTH: 25
<212> TYPE: DNA
<213> ORGANISM: Artificial Sequence
<220> FEATURE:
<223> OTHER INFORMATION: Primer

<400> SEQUENCE: 25
gccaatactt cacaatgttc gaatc                                            25

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
cgtgaatgta agcgtgacat aac                                              23

<210> SEQ ID NO 27
<211> LENGTH: 57
<212> TYPE: DNA
<213> ORGANISM: Artificial Sequence
<220> FEATURE:
<223> OTHER INFORMATION: Primer

<400> SEQUENCE: 27
caaaaagtta acatgcatca ccatcaccat cacactaacc caactaggct cattaac         57

<210> SEQ ID NO 28
<211> LENGTH: 58
<212> TYPE: DNA
<213> ORGANISM: Artificial Sequence
<220> FEATURE:
<223> OTHER INFORMATION: Primer

<400> SEQUENCE: 28
gttatctgca ggttacccag tggtacgaag cgccatcagc catttctgga tcaatttc        58

```
<210> SEQ ID NO 29
<211> LENGTH: 58
<212> TYPE: DNA
<213> ORGANISM: Artificial Sequence
<220> FEATURE:
<223> OTHER INFORMATION: Primer

<400> SEQUENCE: 29
tgccggtctc cctatagtga gtcgtattaa tttcatccag ttccaggtga attataag          58

<210> SEQ ID NO 30
<211> LENGTH: 58
<212> TYPE: DNA
<213> ORGANISM: Artificial Sequence
<220> FEATURE:
<223> OTHER INFORMATION: Primer

<400> SEQUENCE: 30
taactaatta catgactcga ggtcgacggt atcccatact atgcttggca tcttaaac          58

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
ttgatagggc aaattctcca ac                                                22

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ttcacctgga taaccttctg                                                   20

<210> SEQ ID NO 33
<211> LENGTH: 54
<212> TYPE: DNA
<213> ORGANISM: Artificial Sequence
<220> FEATURE:
<223> OTHER INFORMATION: Primer

<400> SEQUENCE: 33
caaaaagtta acatgcatca ccatcaccat cacatgtcct tgcaggtggt attc              54

<210> SEQ ID NO 34
<211> LENGTH: 55
<212> TYPE: DNA
<213> ORGANISM: Artificial Sequence
<220> FEATURE:
<223> OTHER INFORMATION: Primer

<400> SEQUENCE: 34
ttatctgcag gttacccagt ggtacgaagc gccaggtaaa gcgtatggca tgttg             55

<210> SEQ ID NO 35
<211> LENGTH: 57
<212> TYPE: DNA
<213> ORGANISM: Artificial Sequence
<220> FEATURE:
<223> OTHER INFORMATION: Primer
```

```
<400> SEQUENCE: 35
ctgccggtct ccctatagtg agtcgtatta atttcgctgg tgaattccca ttatctg        57

<210> SEQ ID NO 36
<211> LENGTH: 58
<212> TYPE: DNA
<213> ORGANISM: Artificial Sequence
<220> FEATURE:
<223> OTHER INFORMATION: Primer

<400> SEQUENCE: 36
taactaatta catgactcga ggtcgacggt atccataacc atctaaagca ttatagtc      58

<210> SEQ ID NO 37
<211> LENGTH: 22
<212> TYPE: DNA
<213> ORGANISM: Artificial Sequence
<220> FEATURE:
<223> OTHER INFORMATION: Primer

<400> SEQUENCE: 37
aagtttcagc aaatggtttg ac                                             22

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
tatcttgcac ctggataacc                                                20

<210> SEQ ID NO 39
<211> LENGTH: 59
<212> TYPE: DNA
<213> ORGANISM: Artificial Sequence
<220> FEATURE:
<223> OTHER INFORMATION: Primer

<400> SEQUENCE: 39
caaaaagtta acatgcatca ccatcaccat cacaatctaa gaggtaaagt tcaacattc     59

<210> SEQ ID NO 40
<211> LENGTH: 55
<212> TYPE: DNA
<213> ORGANISM: Artificial Sequence
<220> FEATURE:
<223> OTHER INFORMATION: Primer

<400> SEQUENCE: 40
gttatctgca ggttacccag tggtacgaag cgccattggt ttgccgtgtg gattg         55

<210> SEQ ID NO 41
<211> LENGTH: 56
<212> TYPE: DNA
<213> ORGANISM: Artificial Sequence
<220> FEATURE:
<223> OTHER INFORMATION: Primer

<400> SEQUENCE: 41
ctgccggtct ccctatagtg agtcgtatta atttcggagt tcaacaaccg ttcaag        56

<210> SEQ ID NO 42
<211> LENGTH: 54
```

```
<212> TYPE: DNA
<213> ORGANISM: Artificial Sequence
<220> FEATURE:
<223> OTHER INFORMATION: Primer

<400> SEQUENCE: 42
taactaatta catgactcga ggtcgacggt atcatgaagt tgatgctgct ttgg      54

<210> SEQ ID NO 43
<211> LENGTH: 25
<212> TYPE: DNA
<213> ORGANISM: Artificial Sequence
<220> FEATURE:
<223> OTHER INFORMATION: Primer

<400> SEQUENCE: 43
atttagaagc tagaggttca gaaag                                      25

<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44
tagaagaatg accatgccat atag                                       24

<210> SEQ ID NO 45
<211> LENGTH: 73
<212> TYPE: DNA
<213> ORGANISM: Artificial Sequence
<220> FEATURE:
<223> OTHER INFORMATION: Primer

<400> SEQUENCE: 45 tttaattt aatcaaaaag ttaacatgca tcaccatcac catcacactc acagagtcaa   60
ctcctgtata ttc                                                   73

<210> SEQ ID NO 46
<211> LENGTH: 75
<212> TYPE: DNA
<213> ORGANISM: Artificial Sequence
<220> FEATURE:
<223> OTHER INFORMATION: Primer

<400> SEQUENCE: 46
tgaatgtaag cgtgacataa ctaattacat gactcgaggt cgacggtatc tctggcggta 60
ttgaactttg tggag                                                 75

<210> SEQ ID NO 47
<211> LENGTH: 60
<212> TYPE: DNA
<213> ORGANISM: Artificial Sequence
<220> FEATURE:
<223> OTHER INFORMATION: Primer

<400> SEQUENCE: 47
gttatctgca ggttacccag tggtaaagtg tatggatggg ttgaagtatg tctttatatc 60

<210> SEQ ID NO 48
<211> LENGTH: 58
<212> TYPE: DNA
<213> ORGANISM: Artificial Sequence
<220> FEATURE:
```

<223> OTHER INFORMATION: Primer

<400> SEQUENCE: 48
acgaagttat gagctcgaat tcatcgatgc tacccggtgc tgcaaagact ttactaag    58

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
gtgaatggtt aatagtgcgc tatg    24

<210> SEQ ID NO 50
<211> LENGTH: 25
<212> TYPE: DNA
<213> ORGANISM: Artificial Sequence
<220> FEATURE:
<223> OTHER INFORMATION: Primer

<400> SEQUENCE: 50
ctaacaaata ccacttcgac atcag    25

<210> SEQ ID NO 51
<211> LENGTH: 73
<212> TYPE: DNA
<213> ORGANISM: Artificial Sequence
<220> FEATURE:
<223> OTHER INFORMATION: Primer

<400> SEQUENCE: 51
ttttaatttt aatcaaaaag ttaacatgca tcaccatcac catcacacct tccgtgagat    60
ttcccttgtt tac    73

<210> SEQ ID NO 52
<211> LENGTH: 58
<212> TYPE: DNA
<213> ORGANISM: Artificial Sequence
<220> FEATURE:
<223> OTHER INFORMATION: Primer

<400> SEQUENCE: 52
tatacgaagt tatctgcagg ttacccagtg gtataaccca taaccagtga tgttaacc    58

<210> SEQ ID NO 53
<211> LENGTH: 47
<212> TYPE: DNA
<213> ORGANISM: Artificial Sequence
<220> FEATURE:
<223> OTHER INFORMATION: Primer

<400> SEQUENCE: 53
gaagttatga gctcgaattc atcgatgacc actggtgttg ttgatcg    47

<210> SEQ ID NO 54
<211> LENGTH: 75
<212> TYPE: DNA
<213> ORGANISM: Artificial Sequence
<220> FEATURE:
<223> OTHER INFORMATION: Primer

<400> SEQUENCE: 54
tgaatgtaag cgtgacataa ctaattacat gactcgaggt cgacggtatc cgacggtaat    60

```
gaggatgtaa atgag                                              75

<210> SEQ ID NO 55
<211> LENGTH: 25
<212> TYPE: DNA
<213> ORGANISM: Artificial Sequence
<220> FEATURE:
<223> OTHER INFORMATION: Primer

<400> SEQUENCE: 55
aaacaagagc agcatgcaac ttgag                                   25

<210> SEQ ID NO 56
<211> LENGTH: 22
<212> TYPE: DNA
<213> ORGANISM: Artificial Sequence
<220> FEATURE:
<223> OTHER INFORMATION: Primer

<400> SEQUENCE: 56
agtgacacca ggaactctaa ag                                      22

<210> SEQ ID NO 57
<211> LENGTH: 57
<212> TYPE: DNA
<213> ORGANISM: Artificial Sequence
<220> FEATURE:
<223> OTHER INFORMATION: Primer

<400> SEQUENCE: 57
gctttacact ttatgcttcc ggctcctatg ttgaactatg tcaatatcga tcgtatg    57

<210> SEQ ID NO 58
<211> LENGTH: 56
<212> TYPE: DNA
<213> ORGANISM: Artificial Sequence
<220> FEATURE:
<223> OTHER INFORMATION: Primer

<400> SEQUENCE: 58
tatctgcagg ttacccagtg gtacgaagcg ccaaacagaa attggttcat gtgttg     56

<210> SEQ ID NO 59
<211> LENGTH: 56
<212> TYPE: DNA
<213> ORGANISM: Artificial Sequence
<220> FEATURE:
<223> OTHER INFORMATION: Primer

<400> SEQUENCE: 59
gccggtctcc ctatagtgag tcgtattaat ttctggtgta ccaatttggt tatttc     56

<210> SEQ ID NO 60
<211> LENGTH: 58
<212> TYPE: DNA
<213> ORGANISM: Artificial Sequence
<220> FEATURE:
<223> OTHER INFORMATION: Primer

<400> SEQUENCE: 60
atatcagtta ttaccctatg cggtgtgaaa tacacaagta caacaacaac agatttag   58

<210> SEQ ID NO 61
<211> LENGTH: 22
<212> TYPE: DNA
```

```
<213> ORGANISM: Artificial Sequence
<220> FEATURE:
<223> OTHER INFORMATION: Primer

<400> SEQUENCE: 61
tacccacctt tgacataatc ag                                              22

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
attcaaatgg cgtaccttta ac                                              22

<210> SEQ ID NO 63
<211> LENGTH: 55
<212> TYPE: DNA
<213> ORGANISM: Artificial Sequence
<220> FEATURE:
<223> OTHER INFORMATION: Primer

<400> SEQUENCE: 63
gctttacact ttatgcttcc ggctcctatg ttgggactgc tacactccaa atatg          55

<210> SEQ ID NO 64
<211> LENGTH: 59
<212> TYPE: DNA
<213> ORGANISM: Artificial Sequence
<220> FEATURE:
<223> OTHER INFORMATION: Primer

<400> SEQUENCE: 64
ttatctgcag gttacccagt ggtacgaagc gccataatag aagaaacacg tcaaatacc      59

<210> SEQ ID NO 65
<211> LENGTH: 54
<212> TYPE: DNA
<213> ORGANISM: Artificial Sequence
<220> FEATURE:
<223> OTHER INFORMATION: Primer

<400> SEQUENCE: 65
gccggtctcc ctatagtgag tcgtattaat ttccagatca aaccacatca tgag           54

<210> SEQ ID NO 66
<211> LENGTH: 41
<212> TYPE: DNA
<213> ORGANISM: Artificial Sequence
<220> FEATURE:
<223> OTHER INFORMATION: Primer

<400> SEQUENCE: 66
gtagcagtga cgttcattgt gtaatgtgta tatgttttat c                         41

<210> SEQ ID NO 67
<211> LENGTH: 37
<212> TYPE: DNA
<213> ORGANISM: Artificial Sequence
<220> FEATURE:
<223> OTHER INFORMATION: Primer

<400> SEQUENCE: 67
catatacaca ttacacaatg aacgtcactg ctacaac                              37
```

```
<210> SEQ ID NO 68
<211> LENGTH: 53
<212> TYPE: DNA
<213> ORGANISM: Artificial Sequence
<220> FEATURE:
<223> OTHER INFORMATION: Primer

<400> SEQUENCE: 68
atatcagtta ttaccctatg cggtgtgaaa tacacaagca ccaacaccat tac    53

<210> SEQ ID NO 69
<211> LENGTH: 17
<212> TYPE: DNA
<213> ORGANISM: Artificial Sequence
<220> FEATURE:
<223> OTHER INFORMATION: Primer

<400> SEQUENCE: 69
gttgtgcgtg gcttgac                                             17

<210> SEQ ID NO 70
<211> LENGTH: 22
<212> TYPE: DNA
<213> ORGANISM: Artificial Sequence
<220> FEATURE:
<223> OTHER INFORMATION: Primer

<400> SEQUENCE: 70
ataatacagc accaccaact tc                                       22

<210> SEQ ID NO 71
<211> LENGTH: 55
<212> TYPE: DNA
<213> ORGANISM: Artificial Sequence
<220> FEATURE:
<223> OTHER INFORMATION: Primer

<400> SEQUENCE: 71
gctttacact ttatgcttcc ggctcctatg ttgggccatg agatgacttt gtacg   55

<210> SEQ ID NO 72
<211> LENGTH: 57
<212> TYPE: DNA
<213> ORGANISM: Artificial Sequence
<220> FEATURE:
<223> OTHER INFORMATION: Primer

<400> SEQUENCE: 72
ttatctgcag gttacccagt ggtacgaagc gccagttctt gtttgaattc gcgtttg 57

<210> SEQ ID NO 73
<211> LENGTH: 55
<212> TYPE: DNA
<213> ORGANISM: Artificial Sequence
<220> FEATURE:
<223> OTHER INFORMATION: Primer

<400> SEQUENCE: 73
gttatgagct cgaattcatc gatgatatca gggaccgtta attaccaaca atctc   55

<210> SEQ ID NO 74
<211> LENGTH: 25
<212> TYPE: DNA
<213> ORGANISM: Artificial Sequence
<220> FEATURE:
```

<223> OTHER INFORMATION: Primer

<400> SEQUENCE: 74
tgttaattaa ttatttgttt gtttg                                 25

<210> SEQ ID NO 75
<211> LENGTH: 55
<212> TYPE: DNA
<213> ORGANISM: Artificial Sequence
<220> FEATURE:
<223> OTHER INFORMATION: Primer

<400> SEQUENCE: 75
acaaacaaac aaacaaataa ttaattaaca atgtcattgg taatacctca aatag        55

<210> SEQ ID NO 76
<211> LENGTH: 53
<212> TYPE: DNA
<213> ORGANISM: Artificial Sequence
<220> FEATURE:
<223> OTHER INFORMATION: Primer

<400> SEQUENCE: 76
atatcagtta ttaccctatg cggtgtgaaa tacaaagcgg cttgagtaca tgc          53

<210> SEQ ID NO 77
<211> LENGTH: 21
<212> TYPE: DNA
<213> ORGANISM: Artificial Sequence
<220> FEATURE:
<223> OTHER INFORMATION: Primer

<400> SEQUENCE: 77
aactgacgtt tcaagaacat c                                     21

<210> SEQ ID NO 78
<211> LENGTH: 24
<212> TYPE: DNA
<213> ORGANISM: Artificial Sequence
<220> FEATURE:
<223> OTHER INFORMATION: Primer

<400> SEQUENCE: 78
ataaacttgc atttgttgca tacc                                  24

<210> SEQ ID NO 79
<211> LENGTH: 56
<212> TYPE: DNA
<213> ORGANISM: Artificial Sequence
<220> FEATURE:
<223> OTHER INFORMATION: Primer

<400> SEQUENCE: 79
gctttacact ttatgcttcc ggctcctatg ttgaaagtgt aaatagacgt catgag       56

<210> SEQ ID NO 80
<211> LENGTH: 58
<212> TYPE: DNA
<213> ORGANISM: Artificial Sequence
<220> FEATURE:
<223> OTHER INFORMATION: Primer

<400> SEQUENCE: 80
ttatctgcag gttacccagt ggtacgaagc gccactgtgt actaaacgtg ataaatcc     58

```
<210> SEQ ID NO 81
<211> LENGTH: 55
<212> TYPE: DNA
<213> ORGANISM: Artificial Sequence
<220> FEATURE:
<223> OTHER INFORMATION: Primer

<400> SEQUENCE: 81
gttatgagct cgaattcatc gatgatatca gggaccgtta attaccaaca atctc        55

<210> SEQ ID NO 82
<211> LENGTH: 25
<212> TYPE: DNA
<213> ORGANISM: Artificial Sequence
<220> FEATURE:
<223> OTHER INFORMATION: Primer

<400> SEQUENCE: 82
tgttaattaa ttatttgttt gtttg                                         25

<210> SEQ ID NO 83
<211> LENGTH: 54
<212> TYPE: DNA
<213> ORGANISM: Artificial Sequence
<220> FEATURE:
<223> OTHER INFORMATION: Primer

<400> SEQUENCE: 83
aaaacaaaca aacaaacaaa taattaatta acaatgagct ctcatcagtt tttg         54

<210> SEQ ID NO 84
<211> LENGTH: 54
<212> TYPE: DNA
<213> ORGANISM: Artificial Sequence
<220> FEATURE:
<223> OTHER INFORMATION: Primer

<400> SEQUENCE: 84
atatcagtta ttaccctatg cggtgtgaaa tacaagacga tgatgtcttg aatg         54

<210> SEQ ID NO 85
<211> LENGTH: 21
<212> TYPE: DNA
<213> ORGANISM: Artificial Sequence
<220> FEATURE:
<223> OTHER INFORMATION: Primer

<400> SEQUENCE: 85
aactgacgtt tcaagaacat c                                             21

<210> SEQ ID NO 86
<211> LENGTH: 21
<212> TYPE: DNA
<213> ORGANISM: Artificial Sequence
<220> FEATURE:
<223> OTHER INFORMATION: Primer

<400> SEQUENCE: 86
agtaacaatt gcagcaatac c                                             21
```

PICHIA CIFERRII CELLS AND USE THEREOF

FIELD OF THE INVENTION

The invention relates to genetically modified *Pichia ciferrii* cells, to the use thereof and to a method of producing sphingoid bases and sphingolipids.

INCORPORATION BY REFERENCE OF SEQUENCE LISTING

The Sequence Listing in an ASCII text file, named 30707_SequenceListing.txt of 111 KB, created on Feb. 10, 2014, and submitted to the United States Patent and Trademark Office via EFS-Web, is incorporated herein by reference.

PRIOR ART

Since the beginning of the 1960s, *Pichia ciferrii* has been used in the production of sphingoid bases and sphingolipids, cf. Wickerham et al. 1960, J Bacteriol. 80, 484-91.

It is always worth improving the wild-type strain yields of sphingoid bases and sphingolipids.

It was the object of the invention to make available *Pichia ciferrii* cells which have increased productivity regarding sphingoid bases and sphingolipids.

DESCRIPTION OF THE INVENTION

Surprisingly, we found that the cells described hereinbelow having reduced, specific enzyme activities are capable of achieving the object of the invention.

The present invention therefore describes genetically modified *Pichia ciferrii* cells having, in comparison with their wild type, reduced activities of the enzymes as described in the present Claim 1.

The invention further relates to the use of the cells mentioned above and to a method of producing sphingoid bases and sphingolipids.

One advantage of the present invention is that of the cells according to the invention being able to grow to high cell densities.

Another advantage of the present invention is that of the cells producing markedly increased titres of acetylated sphingoid bases when grown in appropriate nutrient media.

A further advantage of the present invention is the high genetic stability of the strains which rules out reversion to the original genotype. Said high genetic stability moreover allows culturing in the absence of antibiotics, since there is no selection pressure to be maintained.

A further advantage of the present invention is the possibility of employing the cells in the biotechnological, environmentally friendly production of sphingoid bases from inexpensive and renewable raw materials.

The present invention relates to a *Pichia ciferrii* cell which is characterized in that the cell has, compared to its wild type, a reduced activity of at least one of the enzymes which are encoded by the intron-free nucleic acid sequences selected from the two groups A) and B) consisting of A) Seq ID No 1, Seq ID No 3, Seq ID No 5, Seq ID No 7, Seq ID No 9, Seq ID No 11, B) a sequence which is at least 80%, particularly preferably at least 90%, additionally preferably at least 95%, and most preferably at least 99%, identical to any of the sequences Seq ID No 1, Seq ID No 3, Seq ID No 5, Seq ID No 7, Seq ID No 9, Seq ID No 11.

In this context, group A) is the nucleic acid sequence group preferred according to the invention.

A "wild type" of a cell means in the context of the present invention preferably the parent strain from which the cell according to the invention has evolved through manipulation of the elements (for example the genes comprising the specified nucleic acid sequences coding for corresponding enzymes or the promoters present in corresponding genes and functionally linked to the nucleic acid sequences specified) that influence the activities of the enzymes encoded by the nucleic acid Seq ID No specified.

The term "activity of an enzyme" in connection with the enzyme encoded by Seq ID No 1 or 3 or by a sequence at least 80%, particularly preferably at least 90%, additionally preferably at least 95%, and most preferably at least 99%, identical to Seq ID No 1 or 3 is always understood as meaning the enzymic activity which catalyses the reaction 5,10-methylenetetrahydrofolate+L-glycine+$H_2O$<=>tetrahydrofolate+L-serine. This activity is preferably determined by the method described in Schlüpen, 2003.

The term "activity of an enzyme" in connection with the enzyme encoded by Seq ID No 5 or by a sequence at least 80%, particularly preferably at least 90%, additionally preferably at least 95%, and most preferably at least 99%, identical to Seq ID No 5 is always understood as meaning the enzymic activity which catalyses the reaction L-serine<=>pyruvate+$NH_3$.

This activity is preferably determined by the method described in Ramos and Wiame, Eur J Biochem. 1982 April; 123(3):571-6.

The term "activity of an enzyme" in connection with the enzyme encoded by Seq ID No 7 or by a sequence at least 80%, particularly preferably at least 90%, additionally preferably at least 95%, and most preferably at least 99%, identical to Seq ID No 7 is always understood as meaning the enzymic activity which catalyses the reaction ATP+sphinganine<=>ADP+sphinganine 1-phosphate.

This activity is preferably determined by the method described in Lanterman and Saba, Biochem J. 1998 Jun. 1; 332 (Pt 2):525-31.

The term "activity of an enzyme" in connection with the enzyme encoded by Seq ID No 9 or by a sequence at least 80%, particularly preferably at least 90%, additionally preferably at least 95%, and most preferably at least 99%, identical to Seq ID No 9 is always understood as meaning the enzymic activity which catalyses the reaction sphinganine 1-phosphate<=>phosphoethanolamine+palmitaldehyde.

This activity is preferably determined by the method described in Van Veldhoven and Mannaerts, J Biol Chem. 1991 Jul. 5; 266(19):12502-7.

The term "activity of an enzyme" in connection with the enzyme encoded by Seq ID No 11 or by a sequence at least 80%, particularly preferably at least 90%, additionally preferably at least 95%, and most preferably at least 99%, identical to Seq ID No 11 is understood as meaning the level of the rate of expression of the enzyme in question, in particular the intracellular concentration. This is determined by 2-D gel technology or Western-blot methods described below.

The wording "reduced activity compared to its wild type" means preferably an activity reduced by at least 50%, particularly preferably by at least 90%, additionally preferably by at least 99.9%, additionally even more preferably by at least 99.99% and most preferably by at least 99.999%, based on the wild-type activity.

Reduction of the particular activities of the cell according to the invention compared to its wild type is determined by above-described methods of determining the activity by employing, where possible, equal cell numbers/concentrations, the cells having been grown under identical conditions such as medium, gassing, agitation, for example. "Nucleotide identity" in relation to the sequences stated may be determined with the aid of known methods. In general, special computer programs with algorithms are used which take into account special requirements.

Preferred methods of determining identity firstly generate the highest agreement between the sequences to be compared. Computer programs for determining identity include but are not limited to the GCG program package including GAP (Deveroy, J. et al., Nucleic Acid Research 12 (1984), page 387, Genetics Computer Group University of Wisconsin, Medicine (Wi), and BLASTP, BLASTN and FASTA (Altschul, S. et al., Journal of Molecular Biology 215 (1990), pages 403-410. The BLAST program may be obtained from the National Center For Biotechnology Information (NCBI) and from other sources (BLAST manual, Altschul S. et al., NCBI NLM NIH Bethesda N. Dak. 22894; Altschul S. et al., supra).

The known Smith-Waterman algorithm may also be used for determining nucleotide identity.

Preferred parameters for determining "nucleotide identity" when using the BLASTN program (Altschul, S. et al., Journal of Molecular Biology 215 (1990), pages 403-410) are:

| | |
|---|---|
| Expect Threshold: | 10 |
| Word size: | 28 |
| Match Score: | 1 |
| Mismatch Score: | −2 |
| Gap costs: | linear |

The above parameters are the default parameters in nucleotide sequence comparison.

The GAP program can also be used with the above parameters.

An identity of 80% according to the above algorithm means in the context of the present invention 80% identity. The same applies to higher identities.

The term "which are encoded by the intron-free nucleic acid sequences" clearly sets out that a sequence comparison involving the sequences stated herein requires the nucleic acid sequences to be compared to be cleared of any introns beforehand.

All percentages (%) are percentages by mass, unless stated otherwise.

Cells preferred according to the invention are characterized in that reduction of the enzymic activity is achieved by modifying at least one gene comprising any of the sequences selected from the nucleic acid sequence groups A) and B) specified hereinabove, the modification being selected from the group comprising, preferably consisting of, insertion of foreign DNA into the gene, deletion of at least parts of the gene, point mutations in the gene sequence, and exposing the gene to the influence of RNA interference, or replacement of parts of the gene with foreign DNA, in particular of the promoter region.

Foreign DNA is understood in this connection as meaning any DNA sequence which is "foreign" to the gene (and not to the organism), i.e. even *Pichia ciferrii* endogenous DNA sequences may act as "foreign DNA" in this connection.

In this context, particular preference is given to the gene being disrupted by insertion of a selection marker gene, thus the foreign DNA being a selection marker gene, in particular one comprising a sequence coding for the *Streptomyces noursei* nat1 gene, which sequence is preferably flanked by the sequence of the *Pichia* PDA1 promoter and the sequence of the *Pichia* TEF terminator, as described in Schorsch et al., 2009; Current Genetics (2009), 55(4), 381-389, for example, the sequence coding for the *Streptomyces noursei* nat1 gene preferably being codon-optimized for *P. ciferrii*, with said insertion preferably having been accomplished by homologous recombination into the gene locus.

In this connection, it may be advantageous for the selection marker gene to be extended by further functionalities which in turn make subsequent removal from the gene possible, which can be achieved, for example, by recombination systems foreign to the organism, such as a Cre/loxP system or FRT (flippase recognition target) system, or the organism's own homologous recombination system.

Preference is given according to the invention to the cell having, compared to its wild type, a combination of reduced activities of the enzymes which are encoded by the intron-free nucleic acid sequences:

Seq ID No 1 or its group B analogue;
Seq ID No 3 or its group B analogue;
Seq ID No 5 or its group B analogue;
Seq ID No 7 or its group B analogue;
Seq ID No 9 or its group B analogue;
Seq ID No 11 or its group B analogue;
Seq ID No 1 or its group B analogue and Seq ID No 3 or its group B analogue;
Seq ID No 1 or its group B analogue and Seq ID No 5 or its group B analogue;
Seq ID No 3 or its group B analogue and Seq ID No 5 or its group B analogue;
Seq ID No 1 or its group B analogue and Seq ID No 3 or its group B analogue and Seq ID No 5 or its group B analogue;
Seq ID No 1 or its group B analogue and Seq ID No 3 or its group B analogue and Seq ID No 5 or its group B analogue and Seq ID No 7 or its group B analogue;
Seq ID No 1 or its group B analogue and Seq ID No 3 or its group B analogue and Seq ID No 5 or its group B analogue and Seq ID No 11 or its group B analogue;
Seq ID No 1 or its group B analogue and Seq ID No 3 or its group B analogue and Seq ID No 5 or its group B analogue and Seq ID No 7 or its group B analogue and Seq ID No 11 or its group B analogue;

In connection with the combinations listed above, preference is given to reducing the enzyme activities encoded by the members of group A.

Cells preferred according to the invention are characterized in that the *Pichia ciferrii* cell derives from strains selected from the group consisting of *Pichia ciferrii* NRRL Y-1031 F-60-10, the *Pichia ciferrii* strains disclosed in the examples of WO 95/12683, and the strain *Pichia ciferrii* CS.PCΔPro2, described in Schorsch et al., 2009, Curr Genet. 55, 381-9.

Cells preferred according to the invention are characterized in that the cell has, compared to its wild type, an increased enzymic activity of at least one of the enzymes selected from an enzyme $E_1$, which catalyses the reaction of serine and palmitoyl-CoA to give 3-ketosphinganine, in particular a serine palmitoyl transferase, in particular those encoded by Seq ID No 13 and/or Seq ID No 15, an enzyme $E_2$, which catalyses the reaction of sphinganine to phytosphinganine, in particular a sphinganine C4-hydroxylase, in particular that encoded by Seq ID No 17.

The term "activity of an enzyme" in connection with the enzyme $E_1$ is always understood as meaning the enzymic activity which catalyses the reactions of palmitoyl-CoA+L-serine<=>CoA+3-dehydro-D-sphinganine+$CO_2$.

This activity is preferably determined by the method described in Zweerink et al., J Biol Chem. 1992 Dec. 15; 267(35):25032-8.

The term "activity of an enzyme" in connection with the enzyme $E_2$ is always understood as meaning the enzymic activity which catalyses the reaction sphinganine+NADPH+$H^+$+$O_2$<=>phytosphingosine+$NADP^+$+$H_2O$.

This activity is preferably determined by the method described in Grilley et al., J Biol Chem. 1998 May 1; 273(18): 11062-8.

The term "increased activity of an enzyme" as used hereinabove and in the comments below in the context of the present invention is preferably understood as meaning increased intracellular activity.

The following comments regarding the increase in enzyme activity in cells apply both to the increase in activity of the enzymes $E_1$ to $_2$ and to all enzymes specified hereinbelow, whose activity may be increased where appropriate.

In principle, an increase in enzymic activity can be achieved by increasing the copy number of the gene sequence(s) coding for the enzyme, by using a strong promoter, by altering the codon usage of the gene, by increasing in various ways the half life of the mRNA or of the enzyme, by modifying the regulation of expression of the gene, or by utilizing a gene or allele coding for a corresponding enzyme with increased activity, and by combining these measures where appropriate. Cells genetically modified according to the invention are generated, for example, by transformation, transduction, conjugation or a combination of these methods with a vector containing the desired gene, an allele of this gene or parts thereof and a promoter enabling the gene to be expressed. Heterologous expression is achieved in particular by integrating the gene or alleles into the chromosome of the cell or an extrachromosomally replicating vector.

An overview of the options for increasing enzyme activity in cells is given for pyruvate carboxylase by way of example in DE-A-100 31 999 which is hereby incorporated by way of reference and whose disclosure forms part of the disclosure of the present invention regarding the options for increasing enzyme activity in cells.

Expression of the enzymes or genes specified hereinabove and all enzymes or genes specified below is detectable with the aid of one- and two-dimensional protein gel fractionation and subsequent optical identification of protein concentration in the gel using appropriate evaluation software.

If the increase in an enzyme activity is based exclusively on an increase in expression of the corresponding gene, the increase in said enzyme activity can be quantified simply by comparing the one- or two-dimensional protein fractionations of wild-type and genetically modified cells. A customary method of preparing the protein gels in the case of bacteria and of identifying the proteins is the procedure described by Hermann et al. (Electrophoresis, 22: 1712.23 (2001). The protein concentration may likewise be analysed by Western-blot hybridization with an antibody specific to the protein to be detected (Sambrook et al., Molecular Cloning: a laboratory manual, 2nd Ed. Cold Spring Harbor Laboratory Press, Cold Spring Harbor, N.Y. USA, 1989) and subsequent optical evaluation using appropriate software for concentration determination (Lohaus and Meyer (1989) Biospektrum, 5: 32-39; Lottspeich (1999), Angewandte Chemie 111: 2630-2647).

Preference is given according to the invention to the cell which, compared to its wild type, has an increased enzymic activity of enzyme $E_1$ having, in comparison with its wild type, a combination of reduced activities of the enzymes encoded by the intron-free nucleic acid sequences:

in the combination of Seq ID No 1 or its group B analogue and Seq ID No 3 or its group B analogue and Seq ID No 5 or its group B analogue, or in the combination of Seq ID No 1 or its group B analogue and Seq ID No 3 or its group B analogue and Seq ID No 5 or its group B analogue and Seq ID No 7 or its group B analogue and Seq ID No 11 or its group B analogue.

Preference is given according to the invention to the cell which, compared to its wild type, has an increased enzymic activity of enzymes $E_1$ and $E_2$ having, in comparison with its wild type, a combination of reduced activities of the enzymes encoded by the intron-free nucleic acid sequences:

Seq ID No 1 or its group B analogue and Seq ID No 3 or its group B analogue and Seq ID No 5 or its group B analogue and Seq ID No 7 or its group B analogue and Seq ID No 11 or its group B analogue.

In one variant embodiment, *P. ciferrii* cells according to the invention are such as those described in WO2006048458 and WO2007131720 and additionally having the changes in enzymic activities described above in connection with the present cells according to the invention.

A further contribution to achieving the object of the invention is made by using the cells according to the invention for producing sphingoid bases and sphingolipids.

The term "sphingoid bases" in the context of the present invention is understood as meaning phytosphingosine, sphingosine, sphingadienine, 6-hydroxysphingosine and sphinganine (dihydrosphingosine), also in the acetylated form, such as for example tetraacetylphytosphingosine, triacetylphytosphingosine, diacetylphytosphingosine, O-acetylphytosphingosine, triacetylsphinganine, diacetylsphinganine, O-acetylsphinganine, triacetylsphingosine, diacetylsphingosine, O-acetylsphingosine, tetraacetyl-6-hydroxysphingosine, triacetyl-6-hydroxysphingosine, diacetyl-6-hydroxysphingosine, O-acetyl-6-hydroxysphingosine, triacetylsphingadienine, diacetylsphingadienine, O-acetylsphingadienine.

The term "sphingolipids" in the context of the present invention is understood as meaning compounds which comprise sphingoid bases covalently linked via an amide bond to a fatty acid. The fatty acid may be saturated or mono- or polyunsaturated. The fatty acid side chain may vary in length. The fatty acid side chain may also have functional groups such as hydroxy groups. Sphingolipids include, for example, phytoceramides, ceramides and dihydroceramides, and the more complex glucosylceramides (cerebrosides) and the inositol phosphorylceramides, mannosylinositol phosphorylceramides and mannosyldiinositol phosphorylceramides. The sphingolipids here also include sphingoid bases linked via an amide bond to an acetyl radical, such as for example N-acetylphytosphingosine, N-acetylsphinganine, N-acetylsphingosine, N-acetyl-6-hydroxysphingosine. These compounds are also known by the term of short-chain ceramides.

The use of the cells according to the invention for producing sphingoid bases and sphingolipids selected from the group consisting of phytosphingosine, sphingosine, sphingadienine, 6-hydroxysphingosine, sphinganine (dihydrosphingosine), tetraacetylphytosphingosine (TAPS), triacetylphytosphingosine, diacetylphytosphingosine, O-acetylphytosphingosine, N-acetylphytosphingosine, triacetylsphinganine (TriASa), diacetylsphinganine, O-acetylsphinganine, N-acetylsphinganine, triacetylsphingosine (TriASo), diacetylsphingosine, O-acetylsphingosine, N-acetylsphingosine, tetraacetyl-6-hydroxysphingosine, triacetyl-6-hydroxysphingosine, diacetyl-6-hydroxysphingosine, O-acetyl-6-hydroxysphingosine, N-acetyl-6-hydroxysphingosine, triacetylsphingadienine, diacetylsphingadienine, O-acetylsphingadienine is particularly advantageous. Very particular preference is given to the use of the cells according to the invention for producing tetraacetylphytosphingosine (TAPS).

A use which is preferred according to the invention is characterized according to the invention in that cells preferred according to the invention, as described above, are used.

*P. ciferrii* cells which are used in particular for producing the above-described sphingosine and sphinganine derivatives are such as those described in WO2006048458 and WO2007131720 and additionally having the changes in enzymic activities described above in connection with the present cells according to the invention.

A further contribution to achieving the object of the invention is made by a method of producing the previously described cell according to the invention, said method comprising the steps of:

I) providing a *Pichia ciferrii* cell, and
II) modifying at least one gene comprising any of the sequences selected from the nucleic acid sequence groups A) and B) specified in Claim 1 by
  insertion of foreign DNA, in particular DNA coding for a selection marker gene, preferably one which can be removed without leaving a trace and which leaves a deletion in the target gene, into the gene,
  deletion of at least parts of the gene,
  point mutations in the gene sequence,
  exposing the gene to the influence of RNA interference, and
  replacement of parts of the gene with foreign DNA, in particular of the promoter region.

A further contribution to achieving the object of the invention is made by a method of producing sphingoid bases and sphingolipids, said method comprising the steps of
  a) contacting the cell according to the invention with a medium including a carbon source,
  b) culturing the cell under conditions which enable the cell to produce sphingoid bases and sphingolipids from said carbon source, and
  c) optionally isolating the sphingoid bases and sphingolipids produced.

Methods preferred according to the invention employ cells specified above as preferred according to the invention.

Carbon sources which may be employed are carbohydrates, such as for example glucose, fructose, glycerol, sucrose, maltose, molasses, or else alcohols, such as for example ethanol, and organic acids, such as for example acetate. Nitrogen sources which may be employed are for example ammonia, ammonium sulphate, ammonium nitrate, ammonium chloride, organic nitrogen compounds (such as yeast extract, malt extract, peptone, corn steep liquor). Inorganic compounds, such as for example phosphate salts, magnesium salts, potassium salts, zinc salts, iron salts and others, may also be employed.

Suitable culturing conditions for *Pichia ciferrii* are known to the skilled worker from WO2006048458 and WO2007131720, for example.

The method according to the invention is particularly suitable for producing tetraacetylphytosphingosines (TAPS).

The Examples listed hereinbelow describe the present invention by way of example, but the embodiments specified in said examples are not intended to limit the invention, the scope of use of which ensues from the entire description and the claims.

The following figures are part of the Examples:
FIG. 1: Design principle of gene deletion cassettes
FIG. 2: Design principle of overexpression cassettes

EXAMPLES

Construction of Gene Deletion Cassettes

Unless stated otherwise, gene deletions were carried out by means of classical "one-step gene replacement", as described in Rothstein 1983, Methods Enzymol 101: 202-211.

Deletion cassettes were constructed by in vivo cloning, ultimately resulting in plasmids which were used as templates for PCR-based amplification of the deletion cassettes. These PCR products were then transformed into *P. ciferrii* with the aim of deleting a particular gene.

The deletion cassettes were constructed by employing the plasmid p426HXT7-6HIS (Hamacher et al., 2000; Microbiology 148, 2783-8) as shuttle vector. p426HXT7-6HIS was first cleaved with BamHI and EcoRI, resulting in a 5.69 kb fragment which was used as backbone for the subsequent cloning steps. Initially, three overlapping DNA fragments were generated by PCR for each *P. ciferrii* deletion cassette: a dominant clonNAT marker, which could later be eliminated again, as the central part (nat1 resistance cassette) (cf. Schorsch et al., Curr Genet. 2009 August; 55(4):381-9), a second fragment of about 500 bp in length, representing the 5'-untranslated region of the ORF to be deleted (promoter region, PR) and with overlap to the start of the clonNAT-marker fragment, and a third fragment of about 500 bp in length, representing the 3'-untranslated region (terminator region, TR) of the ORF to be deleted and with overlap to the end of the clonNAT-marker fragment.

Each deletion cassette was constructed by amplifying by means of PCR the promoter region (PR) and the terminator region (TR) of the gene to be deleted from genomic *P. ciferrii* wild-type DNA, in each case employing gene-specific primers. To this end, primer pairs, P1/P2 for PR and P3/P4 for TR, were used in each case. The primers were chosen so as to have at the 5' end regions of about 30-35 bps in length which were overlapping with the DNA elements to be fused:

| Primer | 5' End overlapping with: |
|---|---|
| P1 | Cloning vector p426HXT7-6HIS |
| P2 | nat1 Resistance cassette (PCR amplicon of plasmid pCS.LoxP.nat1 with primers LPNTL.fw and LPNTL.rv) |
| P3 | nat1 Resistance cassette |
| P4 | Cloning vector p426HXT7-6HIS |

The central fragment (nat1 resistance cassette, Seq ID No 19) was amplified using in each case the primer pair LPNTL.fw (TGGCGCTTCGTACCACTGGGTAAC) and LPNTL.rv (GAAATTAATACGACTCACTATAGG), with plasmid pCS.LoxP.nat1 (Schorsch et al., 2009; Curr. Genet. 55, 381-9) being employed as template (all primer sequences are given in 5'→3' orientation).

The PCR products of primer pairs P1/P2, P3/P4 and LPNTL.fw/LPNTL.rv, together with the p426HXT7-6HIS plasmid previously linearized by digestion with BamHI and EcoRI, were transformed into *S. cerevisiae* strain K26. The PCR products and the linearized vector were joined together in vivo by homologous recombination, causing the linearized vector to be re-circularized and able to be propagated in *S. cerevisiae*. Transformants obtained were selected by means of the marker gene (nat1) on YEPD plates with clonNAT, their DNA was isolated and transformed into *E. coli*, and the plasmids re-isolated therefrom were verified by restriction mapping or sequencing. The deletion cassettes were amplified using the primer pairs 426L.fw (GCTTCCGGCTCCTATGTTG, Seq ID No 23) and 426R.rv (ACCCTATGCGGTGTGAAATAC, Seq ID No 24) or HXT7 (GCCAATACTTCACAATGTTCGAATC, Seq ID No 25) and CYC (CGTGAATGTAAGCGTGACATAAC, Seq ID No 26), unless stated otherwise.

See FIG. 1 for clarification.

To successively delete multiple genes, a marker rescue was performed after each deletion. This was accomplished by transformation with plasmid pCS.opt.Cre (Seq ID. No 20) as described previously (Schorsch et al., Curr Genet. 2009 August; 55(4):381-9). The gene deletions were verified by PCR analyses using genomic DNA of the transformants as template.

The particular gene deletion cassettes of the genes with sequences Seq ID No 1, Seq ID No 3, Seq ID No 5, Seq ID No 7, Seq ID No 9 and Seq ID No 11 were constructed using the primers listed in the table below. For each of the Seq IDs, the first two primers listed (SH11 and SH12 or SH21 and SH22 or C1 and C2 or HXT7-LCB4.fw and LCB4.HXT7.rv or HXT7-DPL1.fw and DPL1.rv2 or ORM-426L.fw and ORM-LPNTL.rv) were used in each case for amplification of PR, with the next two primers listed (SH13 and SH14 or SH23 and SH24 or C3 and C4 or LCB4.rv and LCB4.fw or DPL1.fw2 and CYC-DPL1.rv or ORM-LPNTL.fw2 and ORM-426R.rv) being used for amplification of TR. The last two primers listed in each case (SHMT1.pop-in.fw and SHMT1.veri.rv or SHMT2.pop-in.fw and SHMT2.veri.rv or CHA1.pop-in.fw and CHA1.veri.rv or LCB4.pop-in.fw and LCB4.veri.rv or DPL1.pop-in.fw and DPL1.veri.rv or ORM1.pop-in.fw and ORM.veri.rv) are used for detecting integration or the wild-type allele.

| Gene | Primer name | Sequence (5'->3') |
|---|---|---|
| Seq ID No 1 | SH11 Seq ID No 27 | CAAAAAGTTAACATGCATCACCATCACCATCACACT AACCCAACTAGGCTCATTAAC |
| | SH12 Seq ID No 28 | GTTATCTGCAGGTTACCCAGTGGTACGAAGCGCCA TCAGCCATTTCTGGATCAATTTC |
| | SH13 Seq ID No 29 | TGCCGGTCTCCCTATAGTGAGTCGTATTAATTTCAT CCAGTTCCAGGTGAATTATAAG |
| | SH14 Seq ID No 30 | TAACTAATTACATGACTCGAGGTCGACGGTATCCCA TACTATGCTTGGCATCTTAAAC |
| | SHMT1.pop-in.fw Seq ID No 31 | TTGATAGGGCAAATTCTCCAAC |
| | SHMT1.veri.rv Seq ID No 32 | TTCACCTGGATAACCTTCTG |
| Seq ID No 3 | SH21 Seq ID No 33 | CAAAAAGTTAACATGCATCACCATCACCATCACATG TCCTTGCAGGTGGTATTC |
| | SH22 Seq ID No 34 | TTATCTGCAGGTTACCCAGTGGTACGAAGCGCCAG GTAAAGCGTATGGCATGTTG |
| | SH23 Seq ID No 35 | CTGCCGGTCTCCCTATAGTGAGTCGTATTAATTTCG CTGGTGAATTCCCATTATCTG |
| | SH24 Seq ID No 36 | TAACTAATTACATGACTCGAGGTCGACGGTATCCAT AACCATCTAAAGCATTATAGTC |
| | SHMT2.pop-in.fw Seq ID No 37 | AAGTTTCAGCAAATGGTTTGAC |
| | SHMT2.veri.rv Seq ID No 38 | TATCTTGCACCTGGATAACC |
| Seq ID No 5 | C1 Seq ID No 39 | CAAAAAGTTAACATGCATCACCATCACCATCACAAT CTAAGAGGTAAAGTTCAACATTC |
| | C2 Seq ID No 40 | GTTATCTGCAGGTTACCCAGTGGTACGAAGCGCCA TTGGTTTGCCGTGTGGATTG |
| | C3 Seq ID No 41 | CTGCCGGTCTCCCTATAGTGAGTCGTATTAATTTCG GAGTTCAACAACCGTTCAAG |
| | C4 Seq ID No 42 | TAACTAATTACATGACTCGAGGTCGACGGTATCATG AAGTTGATGCTGCTTTGG |
| | CHA1.pop-in.fw Seq ID No 43 | ATTTAGAAGCTAGAGGTTCAGAAAG |
| | CHA1.veri.rv Seq ID No 44 | TAGAAGAATGACCATGCCATATAG |
| Seq ID No 7 | HXT7-LCB4.fw Seq ID No 45 | TTTTAATTTTAATCAAAAAGTTAACATGCATCACCAT CACCATCACACTCACAGAGTCAACTCCTGTATATTC |
| | LCB4.HXT7.rv Seq ID No 46 | TGAATGTAAGCGTGACATAACTAATTACATGACTCG AGGTCGACGGTATCTCTGGCGGTATTGAACTTTGT GGAG |
| | LCB4. rv Seq ID No 47 | GTTATCTGCAGGTTACCCAGTGGTAAAGTGTATGGA TGGGTTGAAGTATGTCTTTATATC |
| | LCB4.fw Seq ID No 48 | ACGAAGTTATGAGCTCGAATTCATCGATGCTACCCG GTGCTGCAAAGACTTTACTAAG |
| | LCB4.pop-in.fw Seq ID No 49 | GTGAATGGTTAATAGTGCGCTATG |
| | LCB4.veri.rv Seq ID No 50 | CTAACAAATACCACTTCGACATCAG |

-continued

| Gene | Primer name | Sequence (5'->3') |
|---|---|---|
| Seq ID No 9 | HXT7-DPL1.fw<br>Seq ID No 51 | TTTTAATTTTAATCAAAAAGTTAACATGCATCACCAT<br>CACCATCACACCTTCCGTGAGATTTCCCTTGTTTAC |
| | DPL1.rv2<br>Seq ID No 52 | TATACGAAGTTATCTGCAGGTTACCCAGTGGTATAA<br>CCCATAACCAGTGATGTTAACC |
| | DPL1.fw2<br>Seq ID No 53 | GAAGTTATGAGCTCGAATTCATCGATGACCACTGGT<br>GTTGTTGATCG |
| | CYC-DPL1.rv<br>Seq ID No 54 | TGAATGTAAGCGTGACATAACTAATTACATGACTCG<br>AGGTCGACGGTATCCGACGGTAATGAGGATGTAAA<br>TGAG |
| | DPL1.pop-in.fw<br>Seq ID No 55 | AAACAAGAGCAGCATGCAACTTGAG |
| | DPL1.veri.rv<br>Seq ID No 56 | AGTGACACCAGGAACTCTAAAG |
| Seq ID No 11 | ORM-426L.fw<br>Seq ID No 57 | GCTTTACACTTTATGCTTCCGGCTCCTATGTTGAAC<br>TATGTCAATATCGATCGTATG |
| | ORM-LPNTL.rv<br>Seq ID No 58 | TATCTGCAGGTTACCCAGTGGTACGAAGCGCCAAA<br>CAGAAATTGGTTCATGTGTTG |
| | ORM-LPNTL.fw2<br>Seq ID No 59 | GCCGGTCTCCCTATAGTGAGTCGTATTAATTTCTGG<br>TGTACCAATTTGGTTATTTC |
| | ORM-426R.rv<br>Seq ID No 60 | ATATCAGTTATTACCCTATGCGGTGTGAAATACACA<br>AGTACAACAACAACAGATTTAG |
| | ORM1.pop-in.fw<br>Seq ID No 61 | TACCCACCTTTGACATAATCAG |
| | ORM.veri.rv<br>Seq ID No 62 | ATTCAAATGGCGTACCTTTAAC |

Construction of Overexpression Cassettes

Overexpression cassettes were constructed in principle in the same way as the method used for the deletion cassettes. In the case of overexpression cassettes, however, an additional fourth PCR product was generated (promoter fragment, PF), representing a fragment of the PcTDH3 or the PcENO1 promoter. This was later linked in vivo to the nat1 resistance cassette and the third PCR fragment which in this case had an overlap with the start of the ORF to be overexpressed (see FIG. 2).

For overexpression of the gene product Seq ID No 13, the native promoter in *P. ciferrii* was replaced with the PcENO1$^{-584-1}$ (Seq ID No 21) promoter fragment. In contrast, the particular native promoter in *P. ciferrii* was replaced with the PcTDH3$^{-420-1}$ promoter fragment (Seq ID No 22) for overexpression of the gene products Seq ID No 15 and Seq ID No 17.

In principle, three different gene-specific primer pairs were used for constructing the particular overexpression cassettes. The primers were chosen so as to have at the 5' end regions of about 30-35 bps in length which were overlapping with the DNA elements to be fused.

| Primer | 5' End overlapping with: |
|---|---|
| P5 | Cloning vector p426HXT7-6HIS |
| P6 | nat1 Resistance cassette (PCR amplicon of plasmid pCS.LoxP.nat1 with primers LPNTL.fw and LPNTL.rv) |
| P9 | nat1 Resistance cassette |
| P10 | 5'-End of the ORF to be overexpressed |
| P7 | 3'-End of the PcENO1$^{-584-1}$ or PcTDH3$^{-420-1}$ promoter fragment |
| P8 | Cloning vector p426HXT7-6HIS |

The nat1 resistance cassette was amplified using in each case the primer pair LPNTL.fw and LPNTL.rv, with plasmid pCS.LoxP.nat1 (Schorsch et al., 2009; Curr. Genet. 55, 381-9) being employed as template. The PCR products of primer pairs P5/P6, P7/P8, P9/P10 and LPNTL.fw/LPNTL.rv, together with the p426HXT7-6HIS plasmid previously linearized by digestion with HpaI and NgoMIV, were transformed into *S. cerevisiae* strain K26. The PCR products and the linearized vector were joined together in vivo by homologous recombination, causing the linearized vector to be re-circularized and able to be propagated in *S. cerevisiae*. Transformants obtained were selected by means of the marker gene (nat1) on YEPD plates with clonNAT, their DNA was isolated and transformed into *E. coli*, and the plasmids re-isolated therefrom were verified by restriction mapping or sequencing. The overexpression cassettes were amplified using the primer pair "426L.fw & 426R.rv" in each case.

Figure 2:
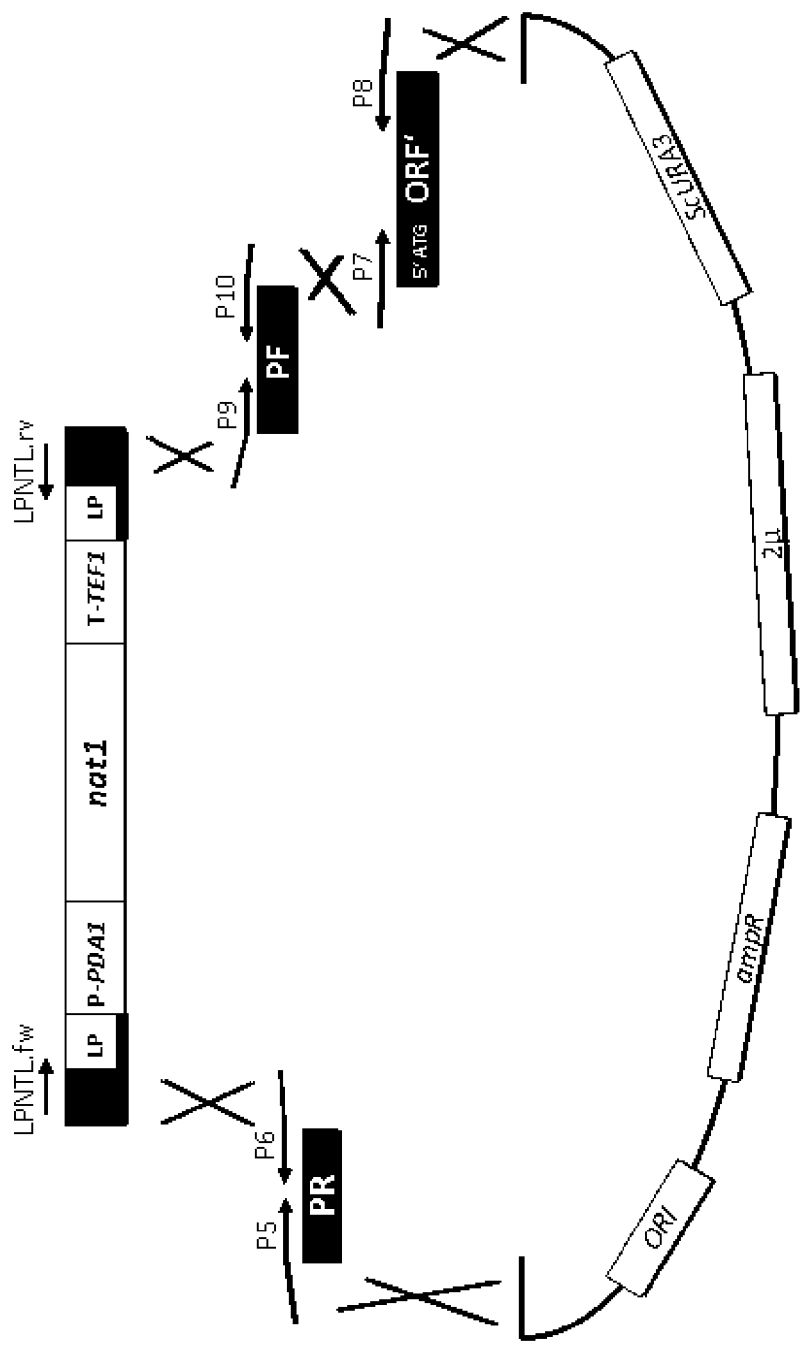

Cf. FIG. 2 for clarification.

For combined overexpression of multiple genes, or for combining overexpressions of one or more target genes with one or more gene deletions, a marker rescue was performed after each step (deletion of a target gene or chromosomal integration of an overexpression cassette). This was accomplished by transformation with plasmid pCS.opt.Cre as described previously (Schorsch et al., Curr Genet. 2009 August; 55(4):381-9). Integration of the overexpression cassettes was verified by PCR analyses using genomic DNA of the transformants as template.

The particular overexpression cassettes for enzymes encoded by the sequences Seq ID No 13, Seq ID No 15 and Seq ID No 17 were constructed using the primers listed in the table below. For each of the Seq IDs, the first two primers listed (LCB1.426L.fw and LCB1.LPNTL.rv or LCB2-426L.fw and LCB2-LPNTL.rv or SYR2oe.426L and SYR2oe.LPNTL.rv) were used in each case for amplification of PR. The next two primers listed (P-ENO.LPNTL.fw and LCB1.P-ENO.rv or TDH3-LPNTL.fw and P-TDH3.rv or TDH3-LPNTL.fw and P-TDH3.rv) were used for amplification of the particular PcENO1$^{-584-1}$ or PcTDH3$^{-420-1}$ promoter fragment. The next two primers listed (P-ENO.LCB1.fw and LCB1.426R.rv or LCB2.P-TDH3.fw and LCB2-426R.rv or SYR2oe.P-TDH3.fw and SYR2oe.426R) were used for amplification of the 5'-ORF fragments of the target genes to be overexpressed in each case. The last two primers listed in each case (P-ENO.veri.rv and LCB1üe.veri.rv or P-TDH3.pop.fw and LCB2üe.veri.rv or P-TDH3.pop.fw and SYR2oe.veri.rv) are used for detecting integration or the wild-type allele.

| Gene | Primer name | Sequence (5'->3') |
|---|---|---|
| Seq ID No 13 | LCB1.426L.fw Seq ID No 63 | GCTTTACACTTTATGCTTCCGGCTCCTATGTTGGGACTGCT ACACTCCAAATATG |
| | LCB1.LPNTL.rv Seq ID No 64 | TTATCTGCAGGTTACCCAGTGGTACGAAGCGCCATAATAG AAGAAACACGTCAAATACC |
| | P-ENO.LPNTL.fw Seq ID No 65 | GCCGGTCTCCCTATAGTGAGTCGTATTAATTTCCAGATCAA ACCACATCATGAG |
| | LCB1.P-ENO.rv Seq ID No 66 | GTAGCAGTGACGTTCATTGTGTAATGTGTATATGTTTTATC |
| | P-ENO.LCB1.fw Seq ID No 67 | CATATACACATTACACAATGAACGTCACTGCTACAAC |
| | LCB1.426R.rv Seq ID No 68 | ATATCAGTTATTACCCTATGCGGTGTGAAATACACAAGCAC CAACACCATTAC |
| | P-ENO.veri.rv Seq ID No 69 | GTTGTGCGTGGCTTGAC |
| | LCB1üe.verisv Seq ID No 70 | ATAATACAGCACCACCAACTTC |
| Seq ID No 15 | LCB2-426L.fw Seq ID No 71 | GCTTTACACTTTATGCTTCCGGCTCCTATGTTGGGCCATGA GATGACTTTGTACG |
| | LCB2-LPNTL.rv Seq ID No 72 | TTATCTGCAGGTTACCCAGTGGTACGAAGCGCCAGTTCTT GTTTGAATTCGCGTTTG |
| | TDH3-LPNTL.fw Seq ID No 73 | GTTATGAGCTCGAATTCATCGATGATATCAGGGACCGTTAA TTACCAACAATCTC |
| | P-TDH3.rv Seq ID No 74 | TGTTAATTAATTATTTGTTTGTTTG |
| | LCB2.P-TDH3.fw Seq ID No 75 | ACAAACAAACAAACAAATAATTAATTAACAATGTCATTGGTA ATACCTCAAATAG |
| | LCB2-426R.rv Seq ID No 76 | ATATCAGTTATTACCCTATGCGGTGTGAAATACAAAGCGGC TTGAGTACATGC |
| | P-TDH3.pop.fw Seq ID No 77 | AACTGACGTTTCAAGAACATC |
| | LCB2üe.veri.rv Seq ID No 78 | ATAAACTTGCATTTGTTGCATACC |
| Seq ID No 17 | SYR2oe.426L Seq ID No 79 | GCTTTACACTTTATGCTTCCGGCTCCTATGTTGAAAGTGTA AATAGACGTCATGAG |
| | SYR2oe.LPNTL.rv Seq ID No 80 | TTATCTGCAGGTTACCCAGTGGTACGAAGCGCCACTGTGT ACTAAACGTGATAAATCC |
| | TDH3-LPNTL.fw Seq ID No 81 | GTTATGAGCTCGAATTCATCGATGATATCAGGGACCGTTAA TTACCAACAATCTC |
| | P-TDH3.rv Seq ID No 82 | TGTTAATTAATTATTTGTTTGTTTG |
| | SYR2oe.P-TDH3.fw Seq ID No 83 | AAAACAAACAAACAAACAAATAATTAATTAACAATGAGCTCT CATCAGTTTTTG |
| | SYR2oe.426R Seq ID No 84 | ATATCAGTTATTACCCTATGCGGTGTGAAATACAAGACGAT GATGTCTTGAATG |
| | P-TDH3.pop.fw Seq ID No 85 | AACTGACGTTTCAAGAACATC |
| | SYR2oe.veri.rv Seq ID No 86 | AGTAACAATTGCAGCAATACC |

Production of Acetylated Sphingoid Bases by the Genetically Modified Strains

Increased titres of acetylated sphingoid bases were achieved by the following genetic modifications:

The tables below depict the titres of acetylated sphingoid bases (tetraacetylphytosphingosine, TAPS and optionally triacetylsphinganine, TriASa) of the different recombinant *P. ciferrii* strains after growth to the stationary phase in a shaker flask.

Details (media used, growth conditions, extraction, quantification by HPLC analysis) are described in Schorsch et al., Curr Genet. 2009 August; 55(4):381-9. The strain employed in the present application corresponds to *Pichia ciferrii* CS.PCΔPro2 designated in the above reference, which is also referred to for short as "CS" hereinbelow.

First, the influence of deletions of various genes on the production of acetylated sphingoid bases was investigated. The results are depicted in the table below. Individually, deletion of PcSHM2 in particular was shown to markedly increase production of acetylated sphingoid bases. This effect was further enhanced by the combination with a PcSHM1 deletion. Further enhancement was achieved by an additional deletion of PcCHA1. This strain, with the relevant genotype of cha1 shm1 shm2, yielded by far the highest titre of 64 mg of TAPS*g−1 (CDW) plus 3 mg of TriASa*g−1 (CDW).

Influence of deletions of various genes on production of acetylated sphingoid bases:

| Strain | Relevant genotype[1] | mg of TAPS * g$^{-1}$ (CDW) | mg of TriASa * g$^{-1}$ (CDW)[2] |
|---|---|---|---|
| CS | | 21 | |
| CS.S1 | shm1 | 20 | |
| CS.S2 | shm2 | 26 | |
| CS.SS | shm1 shm2 | 42 | |
| CS.C | cha1 | 23 | |
| CS.CS1 | cha1 shm1 | 23 | |
| CS.CS2 | cha1 shm2 | 29 | |
| CS.CSS | cha1 shm1 shm2 | 65 | 3 |

[1]Relationship with SEQ-IDs: shm1, SEQ-ID No 1; shm2, SEQ-ID No 3; cha1, SEQ-ID No 5

[2]Titres below 2 mg/g of cell dry mass are not shown.

Next, the influence of various genetic modifications for enhancing enzyme activities were investigated, in the background of strain CS.CSS (cha1 shm1 shm2). For this purpose, the following genetic modifications, both individual and by way of selected combinations, were carried out in the strain CS.CSS:

- deletion of PcLCB4, Seq ID No 7
- deletion of PcDPL1, Seq ID No 9
- deletion of PcORM12, Seq ID No 11
- overexpression of PcLCB1 Seq ID No 13
- overexpression of PcLCB2 Seq ID No 15
- overexpression of PcSYR2 Seq ID No 17.

Moreover, the effects of the deletions of PcLCB4 and PcDPL1 were also addressed alone, that is without combination with the cha1 shm1 shm2 genotype.

To achieve additive or synergistic effects, a multiplicity of the genetic modifications promoting sphingoid base production were combined in different ways in a single strain. The strain with the following genotype turned out to be the best here: cha1 shm1 shm2 lcb4 orm12 TDH3p:LCB2 ENO1p:LCB1 TDH3p:SYR2. This strain produced in a shaker flask a titre of 199 mg of TAPS*g$^{-1}$ (CDW) (plus 12 mg of triacetylsphinganine (TriASa)*g$^{-1}$ (CDW), while the CS reference strain produced only 21 mg of TAPS*g$^{-1}$ (CDW).

The results are depicted in the table below.

Influence of Genetic Modifications of Sphingolipid Metabolism on Production of Acetylated Sphingoid Bases

| Strain | Relevant genotype[1; 2] | mg of TAPS * g$^{-1}$ (CDW) | mg of TriASa * g$^{-1}$ (CDW)[3] |
|---|---|---|---|
| CS | | 21 | |
| CS.L4 | lcb4 | 54 | |
| CS.DPL1 | dpl1 | 28 | |
| CS.S2 | shm2 | 26 | |
| CS.SS | shm1 shm2 | 42 | |
| CS.CSS | cha1 shm1 shm2 | 65 | 3 |
| CSS.L1 | cha1 shm1 shm2 NO1p:LCB1 | 74 | 2 |
| CSS.L2 | cha1 shm1 shm2 TDH3p:LCB2 | 82 | 4 |
| CSS.L1.L2 | cha1 shm1 shm2 ENO1p:LCB1 TDH3p:LCB2 | 102 | 8 |
| CSS.L4 | cha1 shm1 shm2 lcb4 | 116 | 8 |
| CSS.O | cha1 shm1 shm2 orm12 | 104 | 6 |
| CSS.D | cha1 shm1 shm2 dpl1 | 84 | 3 |
| CSS.L4.O | cha1 shm1 shm2 lcb4 orm12 | 172 | 8 |
| CSS.L4.O.L2 | cha1 shm1 shm2 lcb4 orm12 TDH3p:LCB2 | 182 | 16 |
| CSS.L4.O.L2.L1 | cha1 shm1 shm2 lcb4 orm12 TDH3p:LCB2 ENO1p:LCB1 | 178 | 44 |
| CSS.L4.O.L2.L1.S2 | cha1 shm1 shm2 lcb4 orm12 TDH3p:LCB2 ENO1p:LCB1 TDH3p:SYR2 | 199 | 12 |

[1]Relationship with SEQ-IDs: shm1, SEQ-ID No 1; shm2, SEQ-ID No 3; cha1, SEQ-ID No 5; lcb4, SEQ-ID No 7; dpl1, SEQ-ID No 9; orm12, SEQ-ID No 11; LCB1, SEQ-ID No 13; LCB2, SEQ-ID No 15; SYR2, SEQ-ID No 17
[2] Inactivated genes are listed in lower-case letters. Overexpressed genes are listed in capital letters and with the particular promoter (abbreviation "p"), under the control of which they are.
[3]Titres below 2 mg/g of cell dry mass are not shown.

The invention claimed is:

1. An genetically modified *Pichia ciferrii* cell, wherein said genetically modified *Pichia ciferrii* cell has, compared to its wild type, a reduced activity of an $E_1$ enzyme encoded by the intron-free nucleic acid sequences selected from the group consisting of
   A) SEQ ID NO: 1, and
   B) a sequence which is at least 90% identical to SEQ ID NO: 1, wherein said activity of said $E_1$ enzyme is the catalysis of the reaction 5,10-methylenetetrahydrofolate+L-glycine+$H_2O$ to tetrahydrofolate+L-serine.

2. The genetically modified *Pichia ciferrii* cell according to claim 1, wherein said reduction of enzymatic activity is achieved by modifying a gene comprising the nucleic acid sequence set forth in SEQ ID NO: 1, wherein the modification is selected from the group consisting of insertion of foreign DNA into the gene, deletion of at least a portion of the gene, point mutations in the gene sequence, exposing the gene to the influence of RNA interference, and replacement of a portion of the gene with foreign DNA.

3. The genetically modified *Pichia ciferrii* cell according to claim 2, wherein said foreign DNA is a selection marker gene that can be removed without leaving a trace and which leaves a deletion in the target gene.

4. The genetically modified *Pichia ciferrii* cell according to claim 1, wherein the *Pichia ciferrii* cell is obtained from strains selected from the group consisting of
   *Pichia ciferrii* NRRL Y-1031 F-60-10, and
   *Pichia ciferrii* CS.PCΔPro2.

5. The genetically modified *Pichia ciferrii* cell according to claim 1, characterized in that the cell further has, compared to its wild type, an increased enzymatic activity of an enzyme $E_2$, wherein said enzyme $E_2$ catalyzes the reaction of sphinganine to phytosphingosine.

6. A method of producing an isolated *Pichia ciferrii* cell according to claim 1, said method comprising the steps of:
   I) providing an isolated *Pichia ciferrii* cell, and
   II) modifying at least one gene comprising any of the sequences selected from the nucleic acid sequence groups A) and B) specified in claim 1 by insertion of foreign DNA into the gene, deletion of at least parts of the gene, point mutations in the gene sequence, exposing the gene to the influence of RNA interference, and replacement of parts of the gene with foreign DNA.

7. A method of producing sphingoid bases and sphingolipids, said method comprising the steps of
   acting the cell according to claim 1 with a medium including a carbon source,
   b) culturing the cell under conditions which enable the cell to produce sphingoid bases and sphingolipids from said carbon source, and
   c) optionally isolating the sphingoid bases and sphingolipids produced.

8. The genetically modified *Pichia ciferrii* cell according to claim 2, wherein said replacement of a portion of the gene with foreign DNA is of the promoter region.

9. The genetically modified *Pichia ciferrii* cell according to claim 5, wherein said enzyme $E_2$ is a sphinganine C4-hydroxylase.

10. The genetically modified *Pichia ciferrii* cell according to claim 9, wherein said sphinganine C4-hydroxylase is encoded by SEQ ID NO: 17.

11. The method according to claim 6, wherein said foreign DNA is DNA coding for a selection marker gene.

12. The method according to claim 6, wherein said replacement of parts of the gene with foreign DNA is of the promoter region.

13. The genetically modified *Pichia ciferrii* cell of claim 1, wherein said intron-free nucleic acid sequences consists of a sequence that is at least 95% identical to SEQ ID NO: 1.

14. The genetically modified *Pichia ciferrii* cell of claim 13, wherein said intron-free nucleic acid sequences consists of a sequence that is at least 99% identical to SEQ ID NO: 1.

* * * * *